US 010939897B2

(12) United States Patent
Chu et al.

(10) Patent No.: US 10,939,897 B2
(45) Date of Patent: Mar. 9, 2021

(54) HAND-HELD ADHESIVE DELIVER APPARATUS

(71) Applicant: GeneJet Biotech Co., Ltd., Taipei (TW)

(72) Inventors: Fa-Ter Chu, Taipei (TW); Ing-Yuan Lin, New Taipei (TW); Ching-Yi Chen, Taipei (TW); Wen-Yang Lin, New Taipei (TW); Chin-Yu Weng, Chiayi County (TW); Ming-En Sheen, Keelung (TW)

(73) Assignee: GENEJET BIOTECH CO., LTD., Taipei (TW)

( * ) Notice: Subject to any disclaimer, the term of this patent is extended or adjusted under 35 U.S.C. 154(b) by 220 days.

(21) Appl. No.: 16/281,758

(22) Filed: Feb. 21, 2019

(65) Prior Publication Data

US 2020/0268366 A1  Aug. 27, 2020

(51) Int. Cl.
*A61B 17/00* (2006.01)
*A61M 25/00* (2006.01)

(52) U.S. Cl.
CPC .. *A61B 17/00491* (2013.01); *A61B 17/00234* (2013.01); *A61M 25/007* (2013.01); *A61M 2025/0004* (2013.01); *A61M 2025/0076* (2013.01)

(58) Field of Classification Search
CPC ............... A61B 17/00491; A61B 2017/00526
See application file for complete search history.

(56) References Cited

U.S. PATENT DOCUMENTS

| 2013/0178896 A1 | 7/2013 | Stenton |
| 2015/0297207 A1 | 10/2015 | Maxwell et al. |
| 2019/0038271 A1* | 2/2019 | Quintero ............... B65D 47/123 |

FOREIGN PATENT DOCUMENTS

| CN | 101637212 A | 3/2010 |
| CN | 201470527 U | 5/2010 |
| GB | 2501755 A | 5/2014 |

(Continued)

OTHER PUBLICATIONS

Taiwanese Office Action and Search Report dated May 11, 2020 for Application No. 108127292 along with an English translation.

(Continued)

*Primary Examiner* — Wade Miles
*Assistant Examiner* — Mohammed S Adam
(74) *Attorney, Agent, or Firm* — Birch, Stewart, Kolasch & Birch, LLP

(57) ABSTRACT

An adhesive deliver apparatus includes: a separable holder having a flexible press region thereon and comprising an interior receiving chamber for placing the adhesive tube; a support tube having a substantially elongated shape and comprising a proximal end and a distal end; a connector connected with the proximal end of the support tube and arranged to operably connect with a nozzle of the adhesive tube; and an inner tube positioned within the support tube and comprising an inlet end connected with the connector and an outlet end approximating to the distal end of the support tube; wherein when the press region is pressed to cause an interior surface of the press region to press the adhesive tube, the adhesive fluid will be squeezed out from the adhesive tube and transmitted through the inner tube from the inlet end to the outlet end.

18 Claims, 20 Drawing Sheets

(56) References Cited

FOREIGN PATENT DOCUMENTS

TW         201348085 A    12/2013
WO    WO 2019/026028 A1    2/2019

OTHER PUBLICATIONS

Extended European Search Report dated Jan. 29, 2020, for counterpart European Application No. 19190741.9.
Chinese Office Action and Search Report, dated Jan. 7, 2021, for Chinese Application No. 201910708190.5, with an English translation of the Chinese Search Report and a partial English translation of the Chinese Office Action.

* cited by examiner

HAND-HELD ADHESIVE DELIVER APPARATUS

BACKGROUND

The disclosure generally relates to an adhesive deliver apparatus and, more particularly, to a hand-held adhesive deliver apparatus for delivering an adhesive fluid stored in an adhesive tube to a target area.

Various types of adhesives have been developed to fulfill the needs of different applications, such as binding objects, closing wounds, fixing meshes in the surgical treatment, or the like. If the area on which the adhesive needs to be applied cannot be reached or accessed by human hands, a particular adhesive deliver apparatus with an elongated delivery tube is required. For example, US Patent Application Publication No. 2015/0297207 discloses a surgical instrument for dispensing fluid which is stored in a frangible container before use. However, it requires complex mechanical parts to break the frangible container which is typically made of glass. In addition, it also requires complex parts to filter the fragments of the container after the container is opened or broken, so as to prevent the fragments of the container from mixing with the adhesive to be applied. Obviously, those complex mechanical parts not only increase the overall weight of the adhesive dispenser, but also increase the complexity in manufacturing and assembling the adhesive dispenser.

SUMMARY

An example embodiment of an adhesive deliver apparatus for delivering an adhesive fluid contained in an adhesive tube to a target area is disclosed, comprising: a separable holder having a flexible press region thereon and comprising an interior receiving chamber for placing the adhesive tube; a support tube having a substantially elongated shape and comprising a proximal end, a distal end, and a first connection portion, wherein the first connection portion is positioned on an outer surface of the support tube and approximating to the proximal end; a connector connected with the proximal end of the support tube and arranged to operably connect with a nozzle of the adhesive tube; and an inner tube positioned within the support tube and comprising an inlet end connected with the connector and an outlet end approximating to the distal end of the support tube; wherein when the press region is pressed to cause an interior surface of the press region to press the adhesive tube, the adhesive fluid will be squeezed out from the adhesive tube and transmitted through the inner tube from the inlet end to the outlet end.

Another example embodiment of an adhesive deliver apparatus for delivering an adhesive fluid contained in an adhesive tube to a target area is disclosed, comprising: a support tube comprising a proximal end and a distal end; a connector connected with the proximal end of the support tube and arranged to operably connect with a nozzle of the adhesive tube; and an inner tube positioned within the support tube and comprising an inlet end connected with the connector and an outlet end approximating to the distal end of the support tube; wherein the adhesive fluid is transmitted through the inner tube from the inlet end to the outlet end.

Both the foregoing general description and the following detailed description are examples and explanatory only, and are not restrictive of the invention as claimed.

DETAILED DESCRIPTION

Reference is made in detail to embodiments of the invention, which are illustrated in the accompanying drawings. The same reference numbers may be used throughout the drawings to refer to the same or like parts, components, or operations.

Figure 1:
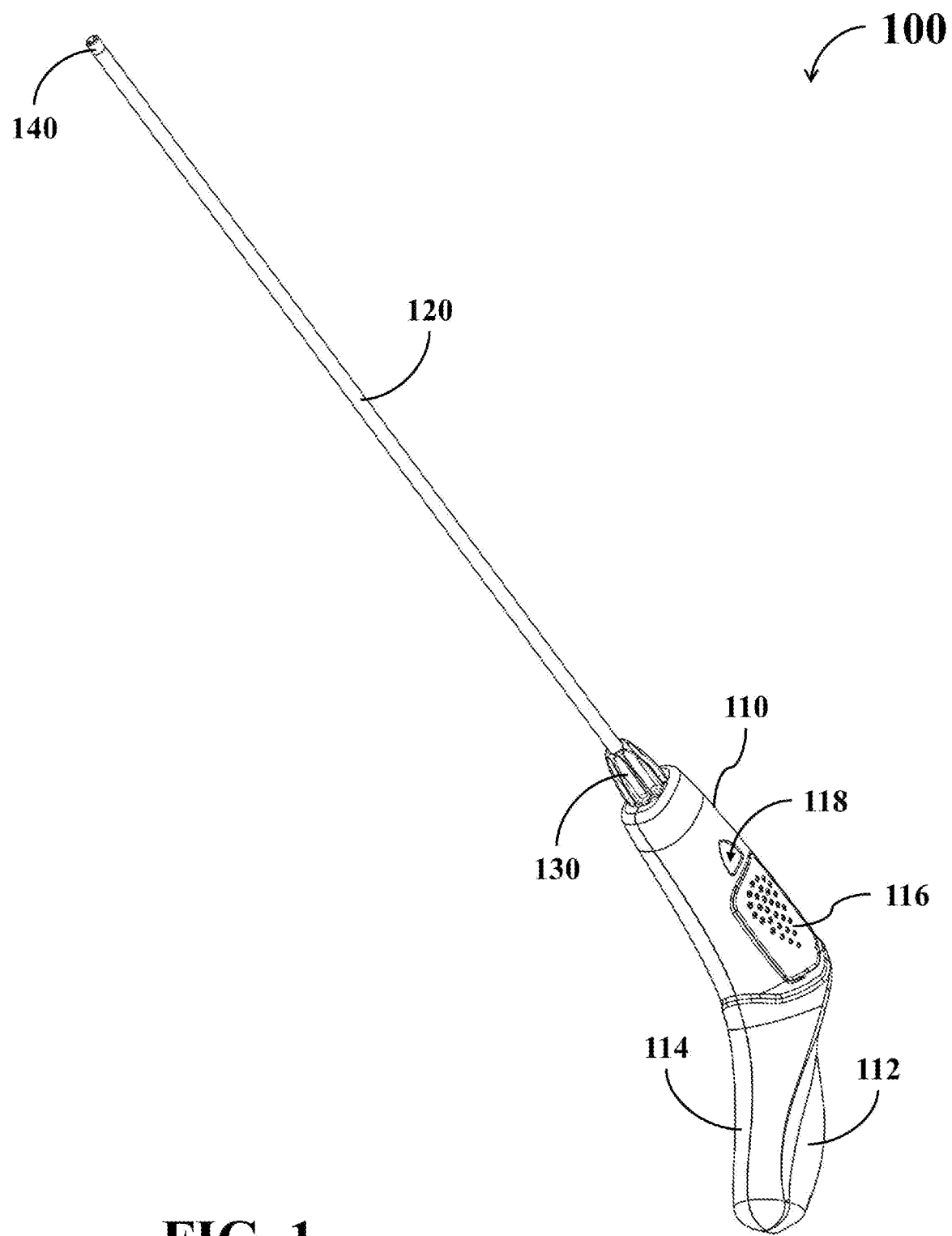
FIG. 1 shows a simplified schematic diagram of a hand-held adhesive deliver apparatus according to a first embodiment.
Figure 2:
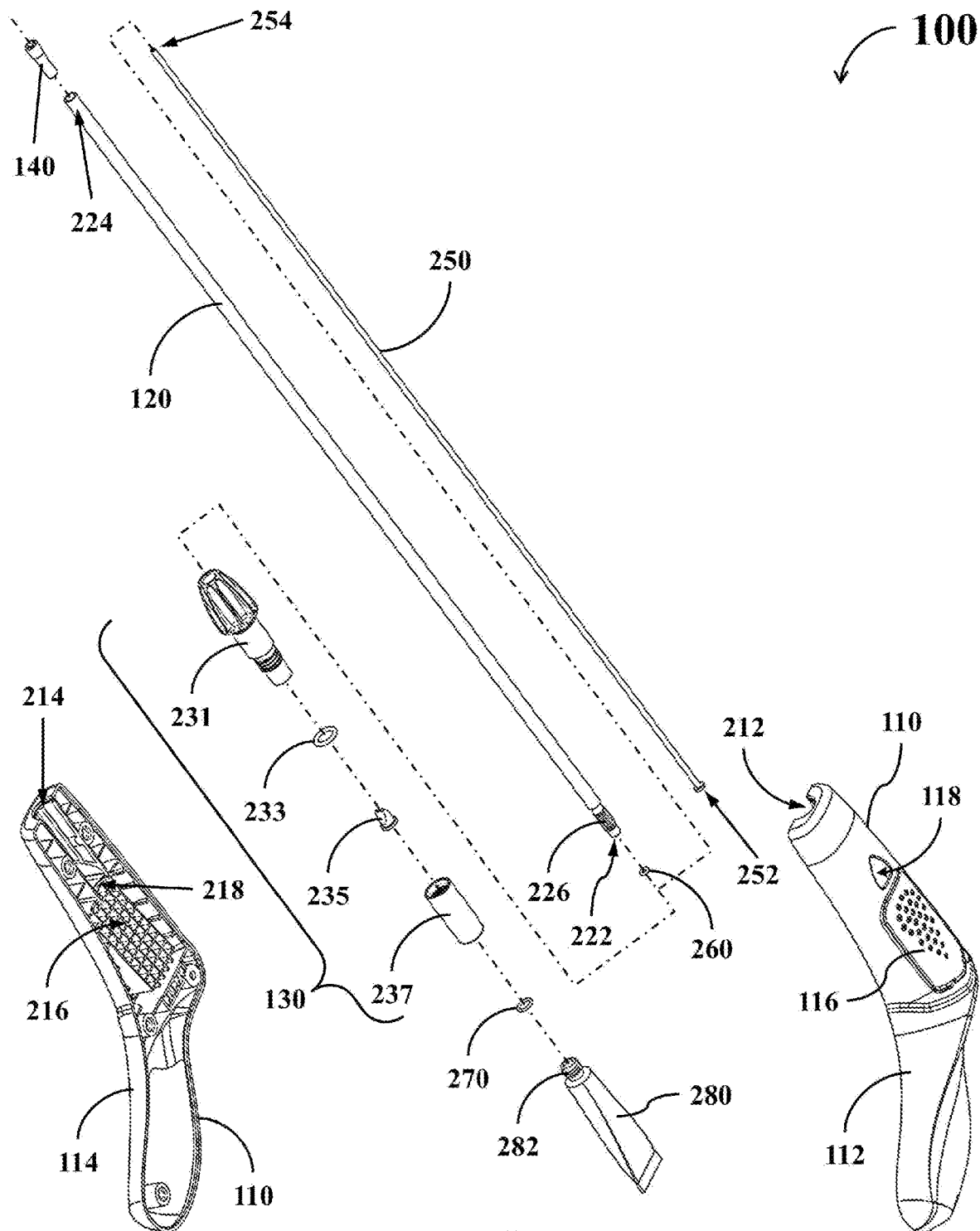
FIG. 2 shows a schematic decomposed diagram of the adhesive deliver apparatus in FIG. 1.

Please refer to FIG. 1 and FIG. 2. FIG. 1 shows a simplified schematic diagram of a hand-held adhesive deliver apparatus 100 according to a first embodiment. FIG. 2 shows a schematic decomposed diagram of the adhesive deliver apparatus 100. The adhesive deliver apparatus 100 can be utilized for delivering an adhesive fluid contained in an adhesive tube 280 to target areas of difficult access.

As shown in FIG. 1 and FIG. 2, the adhesive deliver apparatus 100 comprises a separable holder 110, a support tube 120, a connector 130, a hollow tip element 140, a flexible inner tube 250, a leakproof ring 260, and a leakproof ring 270.

The separable holder 110 comprises a first holder portion 112 and a second holder portion 114, which can be detachably connected with each other to form an L-shaped holder. When the adhesive deliver apparatus 100 is used, the user can move and/or rotate the separable holder 110 to change the adhesive output position. As shown in FIG. 2, a first notch 212 is positioned in the front end of the first holder portion 112, while a second notch 214 is positioned in the front end of the second holder portion 114. When the first holder portion 112 and the second holder portion 114 is assembled together, the first notch 212 and the second notch 214 collectively form an opening through which part of the connector 130 can be inserted into the separable holder 110.

Each of the first holder portion 112 and the second holder portion 114 has a flexible press region 116 and an opening 118 thereon, wherein the flexible press region 116 is deformable when pressed by the user. As shown in FIG. 2, the opening 118 is positioned beside the press region 116 and arranged to operably allow the user to observe the interior of the separable holder 110. In addition, the separable holder 110 also comprises an interior receiving chamber 216 for placing the adhesive tube 280 which contains the adhesive fluid to be applied to the target areas. When the adhesive tube 280 is installed within the receiving chamber 216 inside of the separable holder 110, the adhesive tube 280 is clamped by the first holder portion 112 and the second holder portion 114.

Additionally, each of the first holder portion 112 and the second holder portion 114 further comprises a limiting notch inside respectively. For illustrative purpose, only a limiting notch 218 formed in the interior of the second holder portion 114 is depicted in FIG. 2 as an example. The limiting notch 218 on the second holder portion 114 is positioned beside the receiving chamber 216 and the opening 118 in the separable holder 110. The limiting notch 218 is arranged to operably allow a nozzle 282 of the adhesive tube 280 to pass therethrough, but not allow the main body of the adhesive tube 280 to pass therethrough.

The support tube 120 has a substantially elongated shape and comprises a proximal end 222, a distal end 224, and a first connection portion 226. The first connection portion 226 is positioned on an outer surface of the support tube 120 and approximates to the proximal end 222. The support tube 120 is utilized for protecting the inner tube 250 and for restricting the extending direction of the inner tube 250.

The connector 130 is connected with the proximal end 222 of the support tube 120 and arranged to operably connect with the nozzle 282 of the adhesive tube 280. In practice, the connector 130 may be detachably connected with the proximal end 222, or firmly connected with the proximal end 222. In order to prevent leakage of the adhesive fluid, the leakproof ring 270 can be spaced between the connector 130 and the nozzle 282.

The inner tube 250 is positioned within the support tube 120 and comprises an inlet end 252 and an outlet end 254. The inlet end 252 is connected with the connector 130 and the outlet end 254 is positioned approximating to the distal end 224 of the support tube 120. The inner tube 250 is utilized for transmitting the adhesive fluid from the adhesive tube 280. Since the inner tube 250 is flexible, the extending direction and shape of the inner tube 250 is determined by the support tube 120. An outer flange may be formed at the inlet end 252 of the inner tube 250 in order to prevent the adhesive fluid from entering into the gap between the inner tube 250 and the support tube 120. In assembling, the inner tube 250 may be inserted into the leakproof ring 260 and then inserted into the support tube 120.

The tip element 140 is positioned at the distal end 224 of the support tube 120 and arranged to operably fasten the outlet end 254 of the inner tube 250 at the distal end 224 of the support tube 120.

When assembling the adhesive deliver apparatus 100, as shown in FIG. 2, the tip element 140 is inserted into the distal end 224 of the support tube 120, and the outlet end 254 of the inner tube 250 is inserted into the tip element 140. In this way, the inner tube 250 can be fixed within the support tube 120, and will not easily depart from the support tube 120.

When the press region 116 is pressed to cause an interior surface of the press region 116 to press the adhesive tube 280, the adhesive fluid will be squeezed out from the adhesive tube 280 and transmitted through the inner tube 250 from the inlet end 252 to the outlet end 254. In this embodiment, the adhesive fluid inside the inner tube 250 is to be outputted toward outside of the adhesive deliver apparatus 100 through the tip element 140.

In practice, each of the two terminals of the tip element 140 may be designed to have a rounded corner to prevent the solidified adhesive to stick to either terminal of the tip element 140.

As shown in FIG. 2, the connector 130 of this embodiment comprises a front-end element 231, a leakproof ring 233, a backflow prevention valve 235, and a rear-end element 237. The structure and functions of the connector 130 will be further described in the following by reference to FIG. 3 and FIG. 4.

Figure 3:
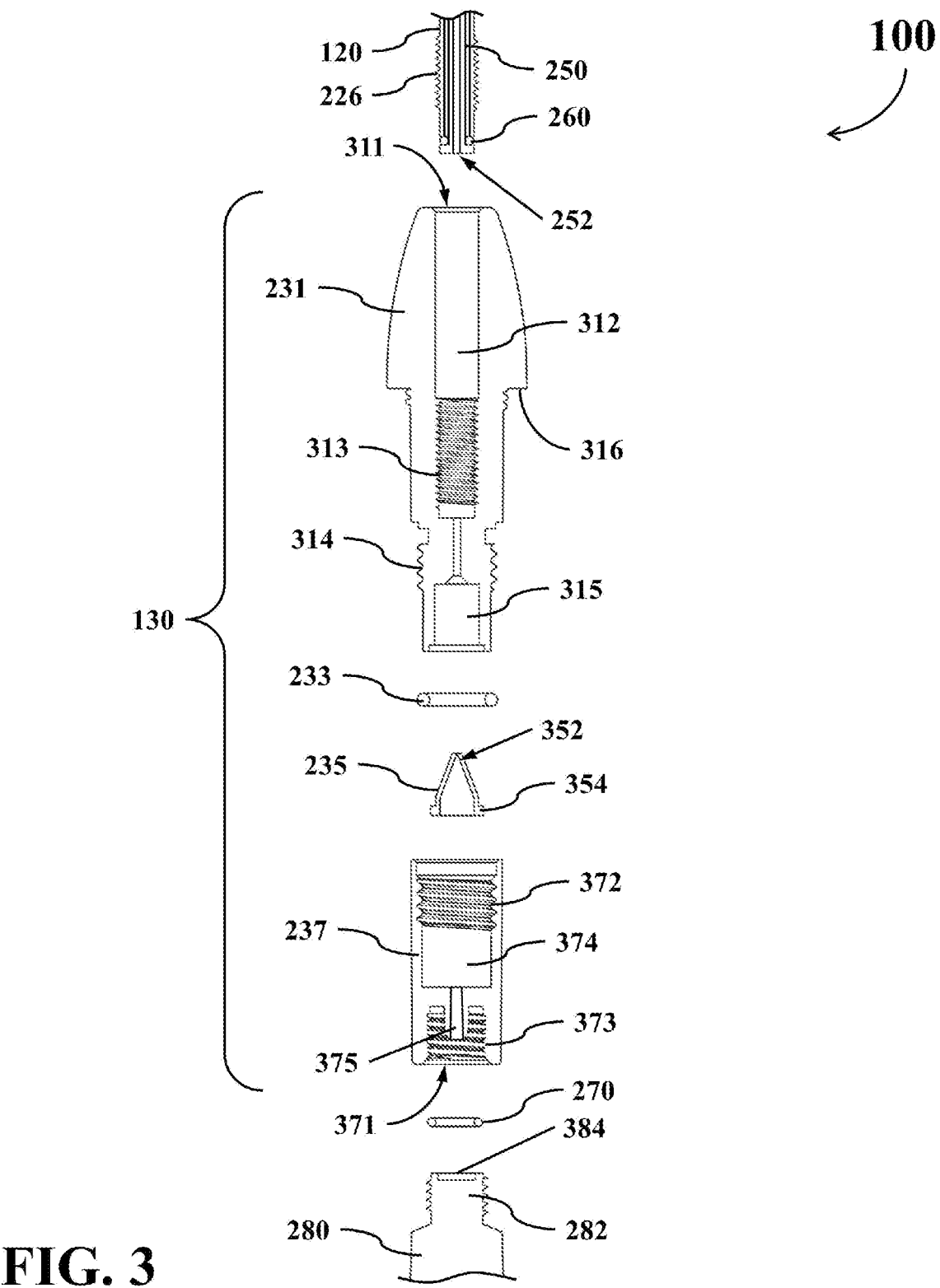
FIG. 3 shows a simplified cross-sectional decomposed diagram of a portion the adhesive deliver apparatus in FIG. 1.
Figure 4:
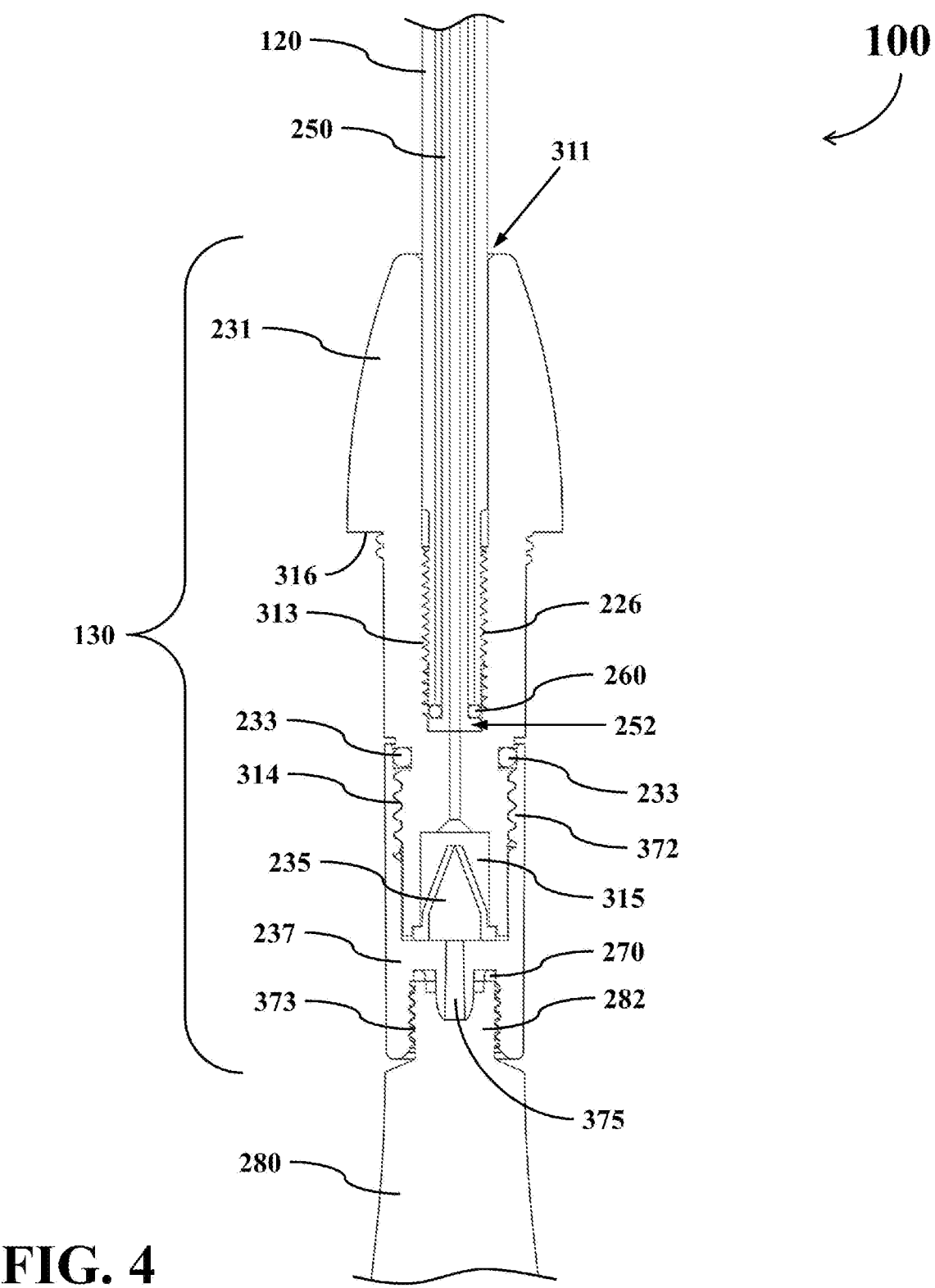
FIG. 4 shows a simplified cross-sectional diagram of a portion the adhesive deliver apparatus in FIG. 1.

FIG. 3 shows a simplified cross-sectional decomposed diagram of a portion of the adhesive deliver apparatus 100. FIG. 4 shows a simplified cross-sectional diagram of a portion of the adhesive deliver apparatus 100 when the support tube 120, the connector 130, the inner tube 250, the leakproof ring 260, the leakproof ring 270, and the adhesive tube 280 are assembled together.

The front-end element 231 is utilized for connecting with the support tube 120. As shown in FIG. 3, the front-end element 231 comprises a front opening 311, a hollow portion 312, a second connection portion 313, a third connection portion 314, a first chamber 315, and a limiting portion 316.

The front opening 311 is positioned on the front end of the front-end element 231, and arranged to operably allow the support tube 120 and the inner tube 250 to insert into the front-end element 231 therethrough. The hollow portion 312 is positioned inside the front-end element 231 for receiving the support tube 120 and the inner tube 250. The second connection portion 313 is formed on the inner surface of the front-end element 231, and arranged to operably engage with the first connection portion 226 of the support tube 120 so as to connect the support tube 120 with the front-end element 231. The third connection portion 314 is positioned near the rear end of the front-end element 231 and formed on the outer surface of the front-end element 231. The first chamber 315 is formed within the rear portion of the front-end element 231, and arranged to operably receive at least part of the backflow prevention valve 235. The limiting portion 316 is protruded outward from the outer surface of the front-end element 231. As shown in FIG. 3, a channel allowing the adhesive fluid to pass therethrough is formed between the first chamber 315 and the hollow portion 312.

The backflow prevention valve 235 is utilized for preventing backflow of the adhesive fluid. As shown in FIG. 3, the backflow prevention valve 235 comprises a duck-bill portion 352 and an outer flange 354.

The duck-bill portion 352 is positioned on the front end of the backflow prevention valve 235, and arranged to operably allow the adhesive fluid to pass from the rear-end element 237 to the first chamber 315 while prevent backflow from the first chamber 315. The flange 354 is formed on the rear end of the backflow prevention valve 235 and extended outward from the backflow prevention valve 235. The flange 354 is arranged to operably define the position between the first chamber 315 and the backflow prevention valve 235, so as to retain the main body of backflow prevention valve 235 to be within the first chamber 315 of the front-end element 231.

The rear-end element 237 is utilized for connecting the front-end element 231 and the adhesive tube 280. The rear-end element 237 comprises a rear opening 371, a fourth connection portion 372, a fifth connection portion 373, a second chamber 374, and a hollow pillar 375.

The rear opening 371 is positioned on the rear end of the rear-end element 237, and arranged to operably allow the nozzle 282 of the adhesive tube 280 to be inserted into the rear-end element 237 therethrough. The fourth connection portion 372 is positioned in the front end of the rear-end element 237, and arranged to operably engage with the third connection portion 314 so as to connect the rear-end element 237 with the front-end element 231. The fifth connection portion 373 is positioned in the rear end of the rear-end element 237, and arranged to operably engage with the nozzle 282 so as to connect the nozzle 282 with the rear-end element 237. The second chamber 374 is formed within the middle section of the rear-end element 237, and arranged to operably receive the first chamber 315 and the backflow prevention valve 235. The hollow pillar 375 is extended from the second chamber 374 toward the rear end of the rear-end element 237.

As shown in FIG. 4, when the above parts of the connector 130 are assembled together, the leakproof ring 233 is sleeved onto the third connection portion 314 of the front-end element 231, and the front-end element 231 is connected with the rear-end element 237 through the engagement between the third connection portion 314 and the fourth connection portion 372. The first chamber 315 of the front-end element 231 is inserted into the second chamber 374 of the rear-end element 237, and the backflow prevention valve 235 is positioned within the first chamber 315. That is, the backflow prevention valve 235 is also positioned within the second chamber 374.

When the nozzle 282 of the adhesive tube 280 is inserted into the rear opening 371 and connected to the fifth connection portion 373, the hollow pillar 375 would break through a nozzle seal 384 on the nozzle 282 and insert into the nozzle 282.

As a result, a fluid transmission channel from the aperture of the hollow pillar 375 to the tip element 140 can be established through the second chamber 374 of the rear-end element 237, the first chamber 315 of the front-end element 231, and the inner tube 250.

As shown in FIG. 3 and FIG. 4, the leakproof ring 260 is spaced between the proximal end 222 of the support tube 120 and the inlet end 252 of the inner tube 250. The use of the leakproof ring 260 can further prevent the adhesive fluid from entering into the gap between the inner tube 250 and the support tube 120. On the other hand, the leakproof ring 233 is spaced between the front-end element 231 and the rear-end element 237, while the leakproof ring 270 is spaced between the rear-end element 237 and the nozzle 282. The use of the leakproof ring 233 and the leakproof ring 270 can further prevent leakage of the adhesive fluid.

In practice, the support tube 120 may be made of rigid materials so as to provide protection to the inner tube 250 inside the support tube 120. For example, the support tube 120 may be realized with various plastic tubes having sufficient rigidness or suitable metal tubes, such as a stainless steel tube.

The inner tube 250 may be made of flexible materials, so that it can be easily fitted inside the support tube 120. For example, the inner tube 250 may be realized with various plastic tubes having higher flexibility, such as silicone tubes, polyethylene tubes, and other suitable tubes.

The first connection portion 226 and the second connection portion 313 may be realized with complementary threaded elements, clamping elements, sleeves, or other suitable engaging elements capable of detachably connecting or permanently connecting the proximal end 222 of the support tube 120 to the front-end element 231 of the connector 130. The third connection portion 314 and the fourth connection portion 372 may be realized with complementary threaded elements, clamping elements, sleeves, or other suitable engaging elements capable of detachably connecting or permanently connecting the front-end element 231 to the rear-end element 237 of the connector 130. Similarly, the fifth connection portion 373 and the nozzle 282 may be realized with appropriately dimensioned threaded elements, clamping elements, sleeves, or other suitable engaging elements capable of detachably connecting or permanently connecting the adhesive tube 280 to the rear-end element 237 of the connector 130.

Each of the leakproof rings 233, 260, and 270 may be realized with various rubber washers, gaskets, flex tapes, or other suitable leakage-proof elements. The backflow prevention valve 235 may be realized with various check valves and ball valve having similar functionalities with the backflow prevention valve 235.

In addition, the adhesive tube 280 for containing the adhesive fluid to be applied is preferably made by deformable and non-frangible materials. For example, the adhesive tube 280 may be realized with various aluminum tubes, plastic tubes, laminated tubes, or other suitable tube that is deformable when pressed or squeezed.

Since the adhesive tube 280 is made of deformable materials, the user can press the press region 116 of the separable holder 110 to extrude the adhesive fluid out of the adhesive tube 280 and apply the extruded adhesive fluid to the target area. When the press region 116 of the separable holder 110 is pressed by the user, the press region 116 is deformed to cause the interior surface of the press region 116 to press the adhesive tube 280. In this situation, the adhesive fluid will be squeezed out from the adhesive tube 280 and then be transmitted through the inner tube 250 from the inlet end 252 to the outlet end 254. The user is allowed to control the amount of adhesive dispensed from the outlet end 254 of the inner tube 250 by manipulating the force applied on the press region 116. As described previously, the adhesive fluid inside the inner tube 250 is to be outputted toward outside of the adhesive deliver apparatus 100 through the tip element 140.

Figure 5:
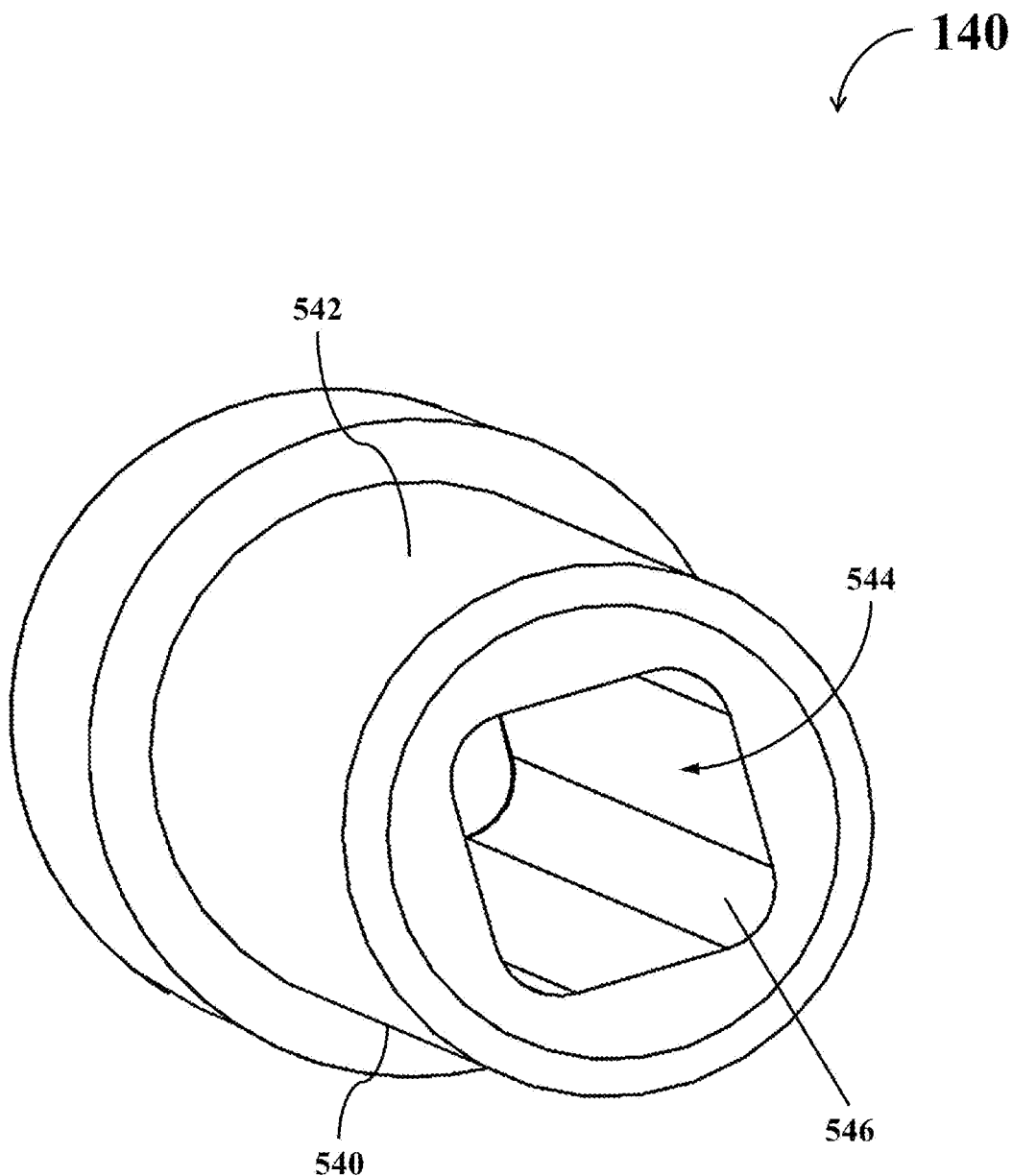
FIG. 5 shows a simplified schematic diagram of a tip element of the hand-held adhesive deliver apparatus in FIG. 1 according to an example embodiment.

Please refer to FIG. 5, which shows a simplified schematic diagram of the tip element 140 of the hand-held adhesive deliver apparatus 100 according to an example embodiment. In this embodiment, the tip element 140 comprises a sleeve portion 540. The sleeve portion 540 has an outer surface 542, a connecting hole 544, and an inner surface 546 positioned within the connecting hole 544.

When the sleeve portion 540 of the tip element 140 is inserted into the distal end 224 of the support tube 120, the outer surface 542 of the sleeve portion 540 is engaged with the inner surface of the support tube 120 to connect the tip element 140 with the support tube 120. When the outlet end 254 of the inner tube 250 is inserted into the connecting hole 544 of the sleeve portion 540, the inner surface 546 of the sleeve portion 540 is engaged with the outer surface of the inner tube 250 to connect the tip element 140 with the inner tube 250.

In the embodiment of FIG. 5, the connecting hole 544 of the tip element 140 is designed to have a cross-section of a rounded square shape. In other embodiment, the connecting hole 544 of the tip element 140 may be designed to have a cross-section of other non-round shapes. For example, the connecting hole 544 of the tip element 140 may be designed to have a cross-section of a hexagonal shape, a pentagonal shape, an octagonal shape, a petal shape, other polygonal shapes, or irregular shapes.

As a result, when the outlet end 254 of the inner tube 250 is inserted into the connecting hole 544 of the sleeve portion 540, only a portion of the inner surface 546 of the sleeve portion 540 would contact with the outer surface of the inner tube 250 while the remaining portions of the inner surface 546 does not contact with the outer surface of the inner tube 250. In this situation, one or more air channels are formed between the tip element 140 and the inner tube 250. These air channels allow sterilization gas to be filled into the gap between the inner tube 250 and the support tube 120 during the manufacturing process of the adhesive deliver apparatus 100.

Figure 6:
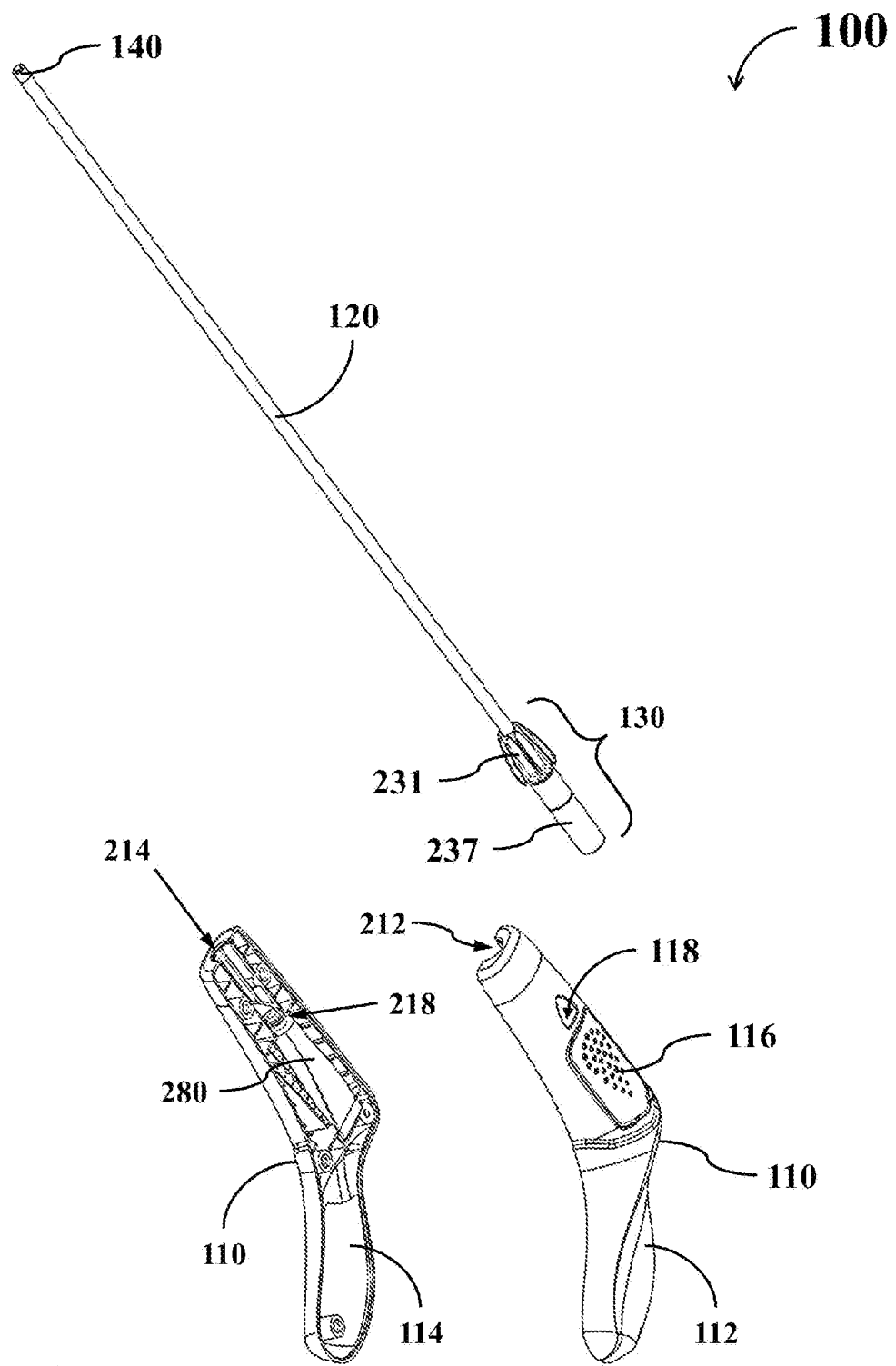
FIG. 6 shows a schematic decomposed diagram of the adhesive deliver apparatus in FIG. 1 when some parts thereof are assembled.
Figure 7:
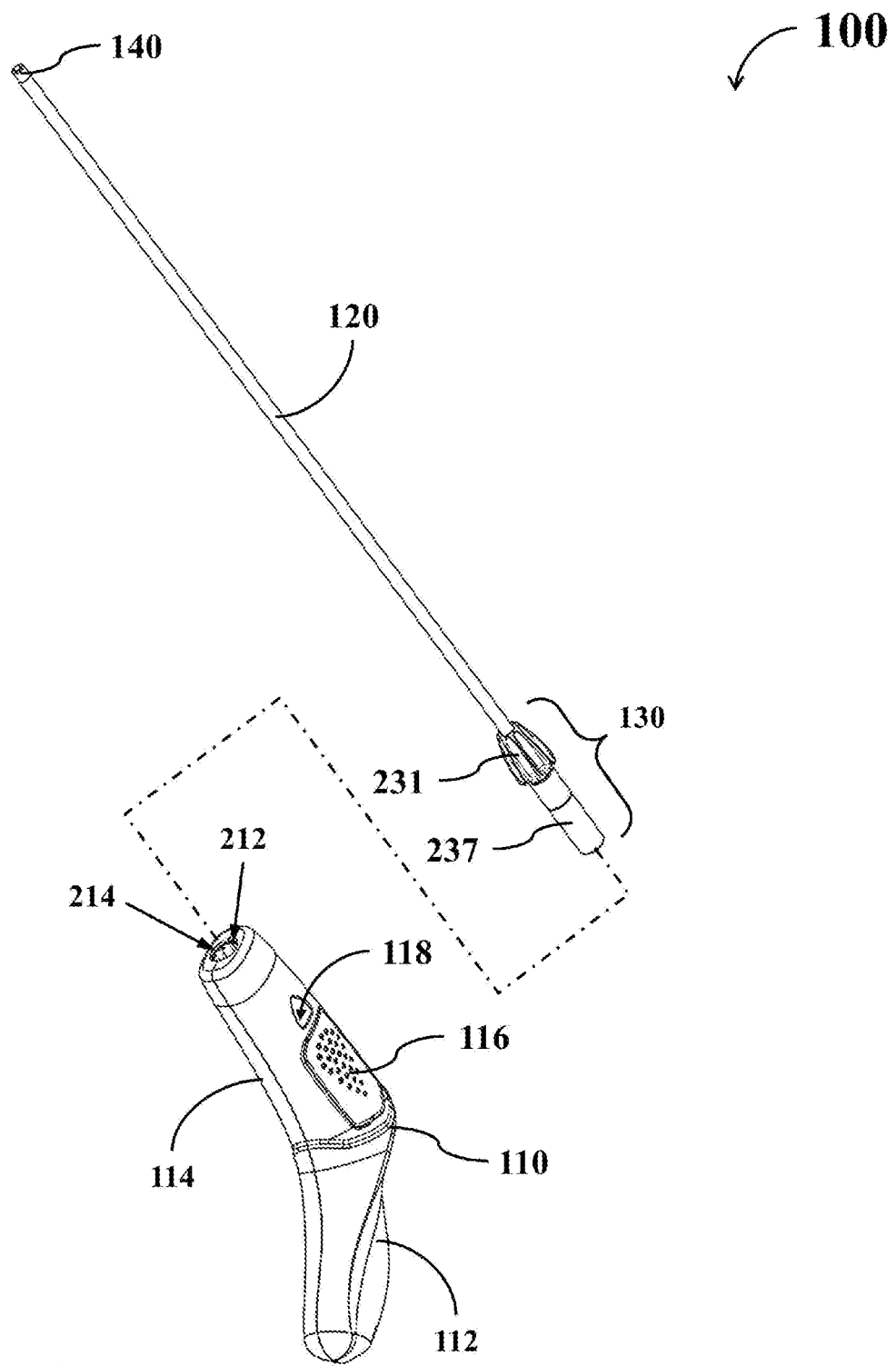
FIG. 7 shows a schematic decomposed diagram of the adhesive deliver apparatus in FIG. 1 when some parts thereof are assembled.

Please refer to FIG. 6 and FIG. 7, which show schematic decomposed diagrams of the adhesive deliver apparatus 100 when some parts thereof are assembled together.

Before the adhesive deliver apparatus 100 is used, the support tube 120, the connector 130, the tip element 140, and the inner tube 250 may be assembled together to form a first part of the adhesive deliver apparatus 100. On the other hand, a new adhesive tube 280 and the separable holder 110 may be assembled together to form a second part of the adhesive deliver apparatus 100.

As described previously, when the adhesive tube 280 is placed within the receiving chamber 216 inside the separable holder 110, the adhesive tube 280 is clamped by the first holder portion 112 and the second holder portion 114. In addition, the limiting notch 218 inside the separable holder 110 does not allow the main body of the adhesive tube 280 to pass therethrough. Accordingly, the adhesive tube 280 can be secured within the separable holder 110 and will not depart from the separable holder 110 through the opening collectively formed by the first notch 212 and the second notch 214.

As shown in FIG. 7, when the user wants to use the adhesive deliver apparatus 100, the user may assemble the aforementioned first part and second part together to form a complete adhesive deliver apparatus 100. Specifically, the user may insert the connector 130 of the above first part into the opening collectively formed by the first notch 212 and the second notch 214 of the second part, and then rotate the connector 130 so that the connector 130 can be connected with the nozzle 282 of the adhesive tube 280. As a result, the hollow pillar 375 of the connector 130 would break through the nozzle seal 384 on the nozzle 282 and insert into the nozzle 282.

During the assembling process, the user is enabled to observe the engagement situation between the connector 130 and the nozzle 282 through the opening 118, so that the assembling process of the adhesive deliver apparatus 100 can be well controlled by the user. On the other hand, the limiting portion 316 of the connector 130 would restrict the relative position between the connector 130 and the separable holder 110. Accordingly, it prevents the rear-end element 237 of the connector 130 or the nozzle 282 from being damaged due to over-insertion of the connector 130.

After completing the assembling of the adhesive deliver apparatus 100, the user can manipulate the separable holder 110 to move the tip element 140 to a target area on which the adhesive fluid needs to be applied. The user can press the press region 116 of the separable holder 110 to squeeze the adhesive fluid out from the adhesive tube 280, so that the adhesive fluid contained in the adhesive tube 280 can enter into the inlet end 252 of the inner tube 250 and be transmitted to the outlet end 254 of the inner tube 250 through the inner tube 250. As described previously, the adhesive fluid inside the inner tube 250 will be outputted toward the target area through the tip element 140.

Afterwards, when the user stops pressing the press region 116 of the separable holder 110, the press region 116 will restore to its original position, and the shape of the deformable adhesive tube 280 may be restored slightly if the adhesive tube 280 is made by materials with some elasticity. In this situation, a small suction force will be generated within the adhesive tube 280 or the fluid transmission channel described above by the slight restoration force of the adhesive tube 280. As a result, the adhesive fluid will be retained within the inner tube 250 and the tip element 140 to prevent the adhesive fluid from dripping out of the tip element 140 when the user stops pressing the press region 116 of the separable holder 110.

Figure 8:
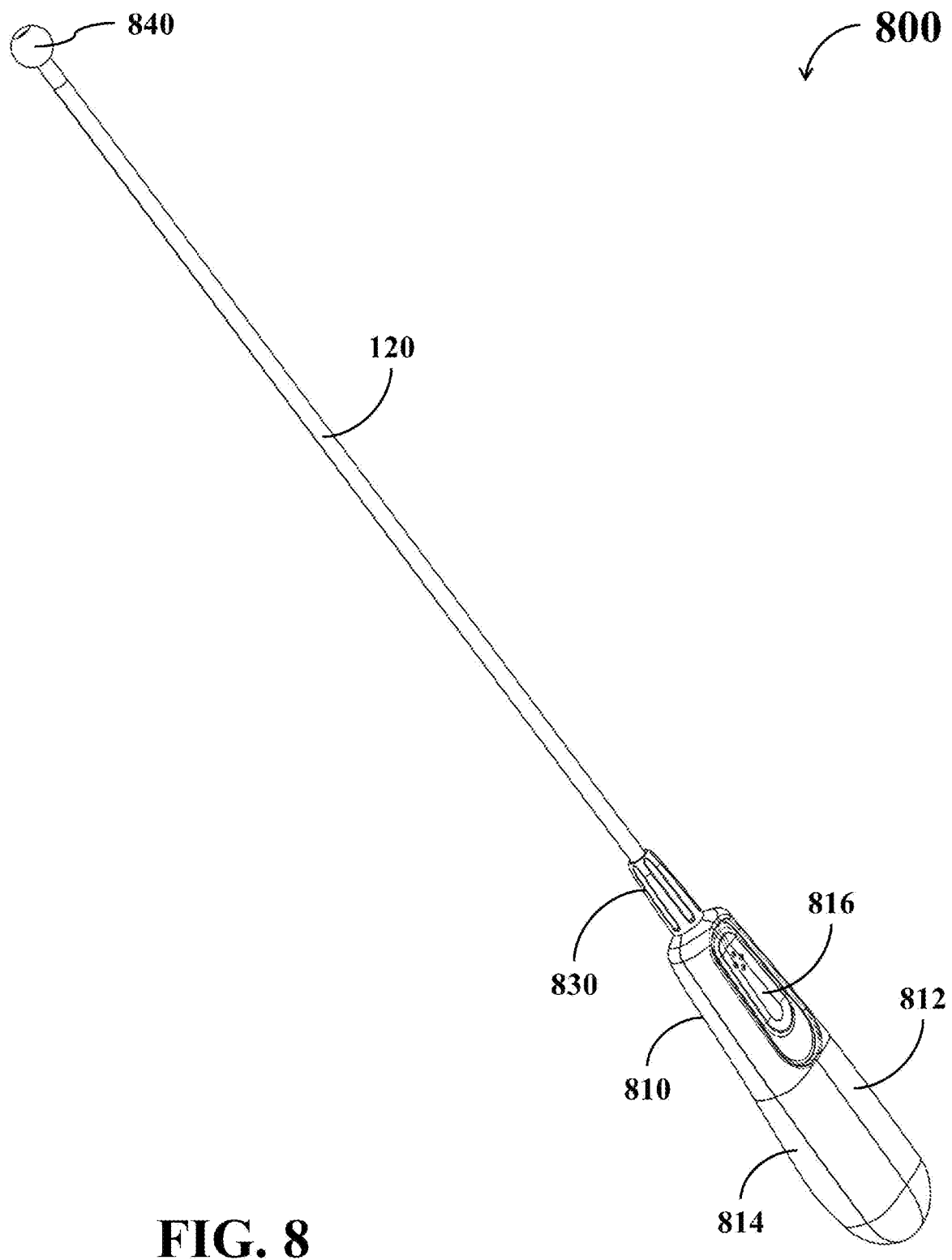
FIG. 8 shows a simplified schematic diagram of a hand-held adhesive deliver apparatus according to a second embodiment.
Figure 9:
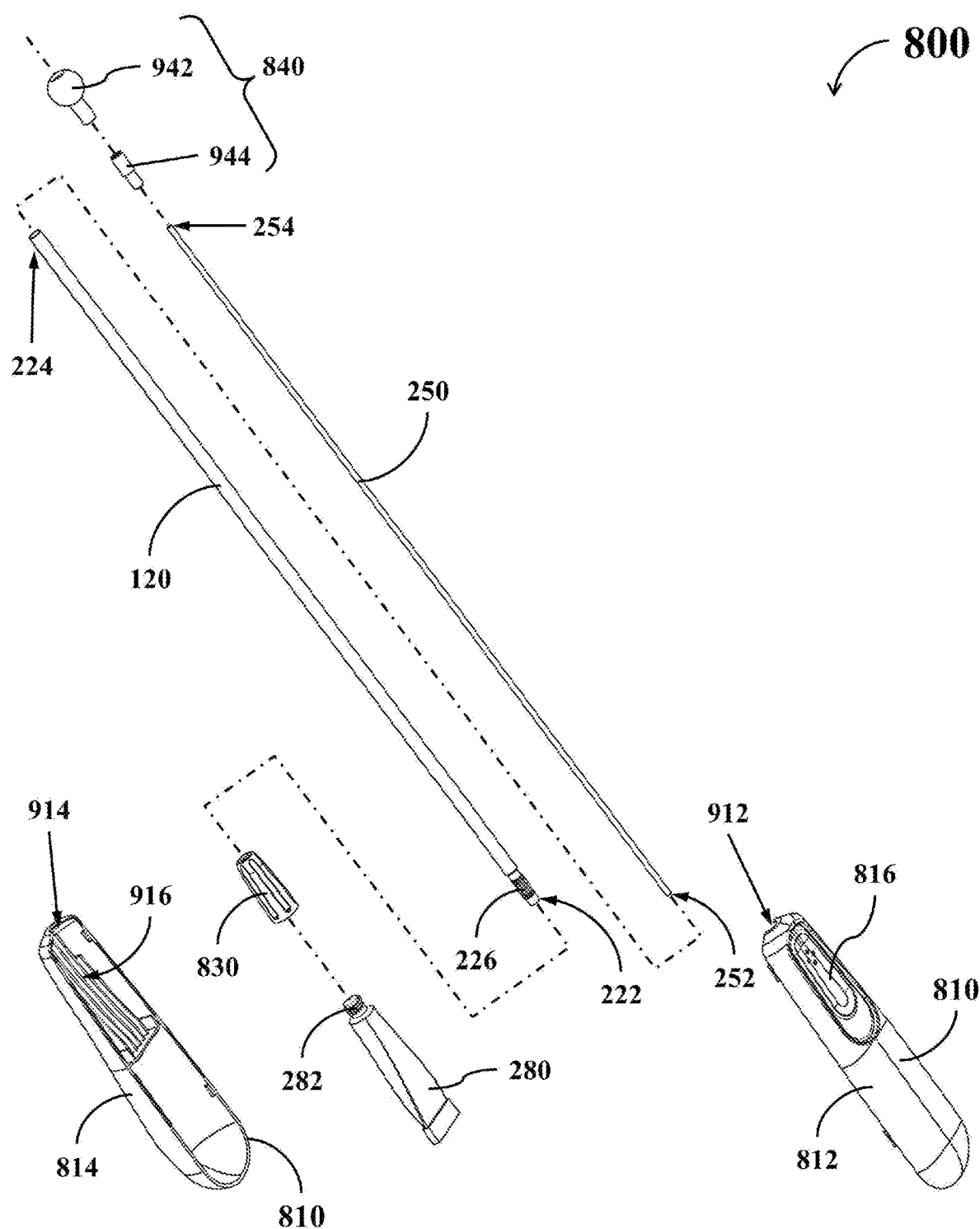
FIG. 9 shows a schematic decomposed diagram of the adhesive deliver apparatus in FIG. 8.

Please refer to FIG. 8 and FIG. 9. FIG. 8 shows a simplified schematic diagram of a hand-held adhesive deliver apparatus 800 according to a second embodiment. FIG. 9 shows a schematic decomposed diagram of the adhesive deliver apparatus 800. The adhesive deliver apparatus 800 can also be utilized for delivering an adhesive fluid contained in the adhesive tube 280 to target areas of difficult access.

As shown in FIG. 8 and FIG. 9, the adhesive deliver apparatus 800 comprises a separable holder 810, a support tube 120, a connector 830, a hollow tip element 840, and an inner tube 250.

The separable holder 810 comprises a first holder portion 812 and a second holder portion 814, which can be detachably connected with each other to form a holder as illustrated in FIG. 8. When the adhesive deliver apparatus 800 is used, the user can manipulate the separable holder 810 to change the adhesive output position. As shown in FIG. 9, a first notch 912 is positioned in the front end of the first holder portion 812, while a second notch 914 is positioned in the front end of the second holder portion 814. When the first holder portion 812 and the second holder portion 814 is assembled together, the first notch 912 and the second notch 914 collectively form an opening through which part of the adhesive tube 280 can be extended outward from the separable holder 810. In this embodiment, for example, the opening collectively formed by the first notch 912 and the second notch 914 is arranged to operably allow the nozzle 282 of the adhesive tube 280 to pass therethrough, but not allow the main body of the adhesive tube 280 to pass therethrough.

Additionally, the first holder portion 812 has a flexible press region 816 thereon, and the flexible press region 816 is deformable when pressed by the user. In addition, the separable holder 810 also comprises an interior receiving chamber 916 for placing the adhesive tube 280 described above. When the adhesive tube 280 is installed within the receiving chamber 916 of the separable holder 810, the adhesive tube 280 is clamped by the first holder portion 812 and the second holder portion 814.

The support tube 120 and the inner tube 250 in the embodiment of FIG. 8 and FIG. 9 are similar to the corresponding components in the adhesive deliver apparatus 100, except that the outer flange formed at the inlet end 252 of the inner tube 250 and the leakproof ring 260 in the adhesive deliver apparatus 100 are omitted in this embodiment. The foregoing descriptions regarding the implementations and components of the support tube 120 and the inner tube 250 in previous embodiments are also applicable to this embodiment. For the sake of brevity, those descriptions will not be repeated here.

The connector 830 is connected with the proximal end 222 of the support tube 120 and the inlet end 252 of the inner tube 250. Additionally, the connector 830 is also arranged to operably connect with the nozzle 282 of the adhesive tube 280. In practice, the connector 830 may be detachably connected with the proximal end 222, or firmly connected with the proximal end 222. Similarly, the connector 830 may be detachably connected with the inlet end 252, or firmly connected with the inlet end 252.

The tip element 840 is positioned at the distal end 224 of the support tube 120 and arranged to operably fasten the outlet end 254 of the inner tube 250 at the distal end 224 of the support tube 120.

As shown in FIG. 9, the tip element 840 of this embodiment comprises a rounded outlet element 942 and a fastening element 944.

The rounded outlet element 942 is positioned at the distal end 224 of the support tube 120 and having a rounded shape. In addition, the rounded outlet element 942 has an outlet aperture with a rounded edge.

The fastening element 944 connects the rounded outlet element 942 with the distal end 224 of the support tube 120.

When assembling the adhesive deliver apparatus 800, as shown in FIG. 9, the outlet end 254 of the inner tube 250 is inserted into a first terminal of the fastening element 944 of the tip element 840, and the first terminal of the fastening element 944 is inserted into the distal end 224 of the support tube 120. On the other hand, a second terminal of the fastening element 944 is inserted into or sleeved onto a connection portion of the rounded outlet element 942, so that the rounded outlet element 942 is positioned at the distal end 224 of the support tube 120. In this way, the inner tube 250 can be fixed within the support tube 120, and will not easily depart from the support tube 120.

When the press region 816 is pressed to cause an interior surface of the press region 816 to press the adhesive tube 280, the adhesive fluid will be squeezed out from the adhesive tube 280 and transmitted through the inner tube 250 from the inlet end 252 to the outlet end 254. In this embodiment, the adhesive fluid inside the adhesive deliver apparatus 800 is dispensed through the inner tube 250, the fastening element 944 and the rounded outlet element 942.

As shown in FIG. 9, the connector 830 of this embodiment is an one-piece component. The inner structure of the connector 830 will be further described in the following by reference to FIG. 10 and FIG. 11.

Figure 10:
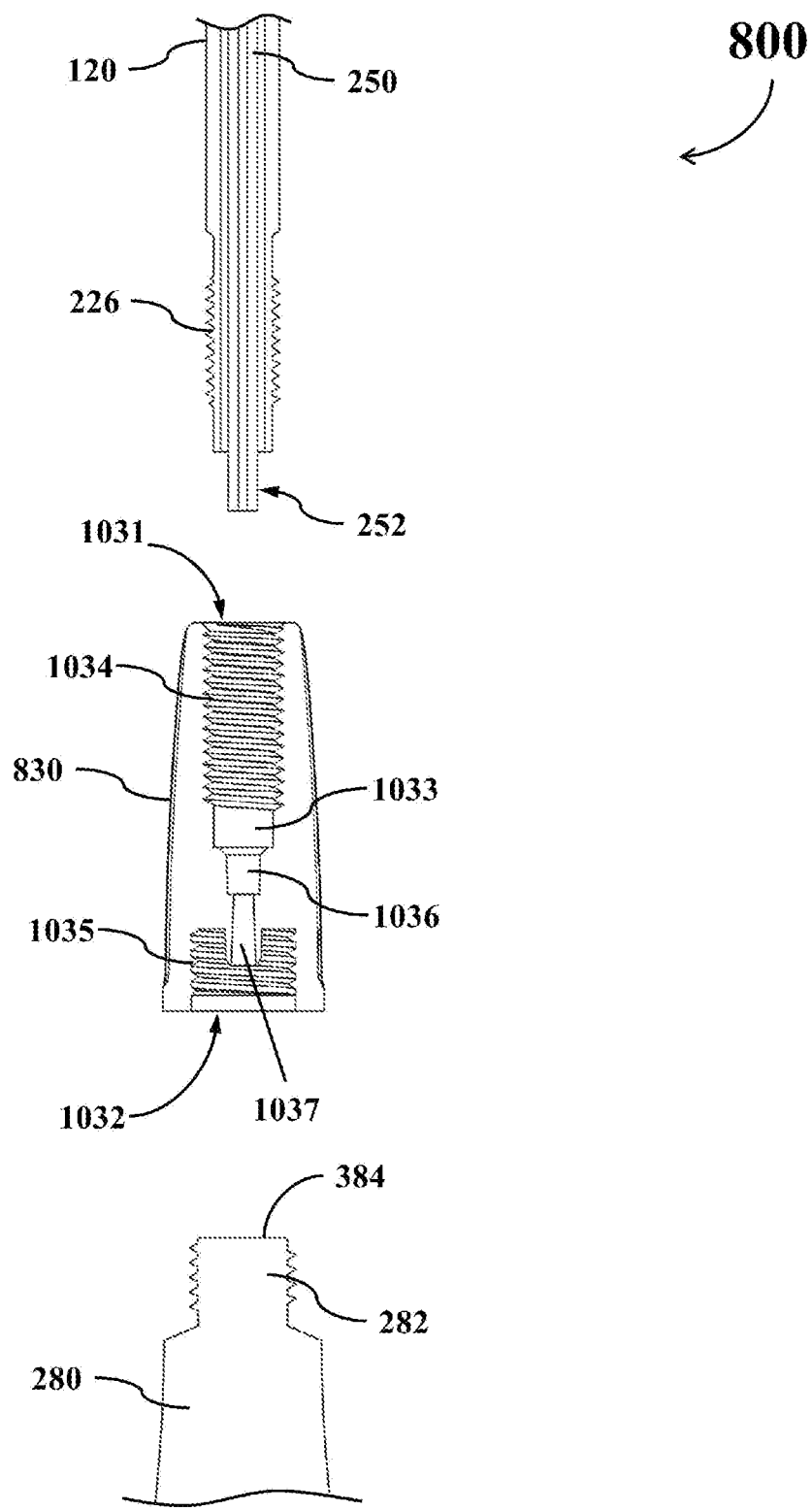
FIG. 10 shows a simplified cross-sectional decomposed diagram of a portion the adhesive deliver apparatus in FIG. 8.
Figure 11:
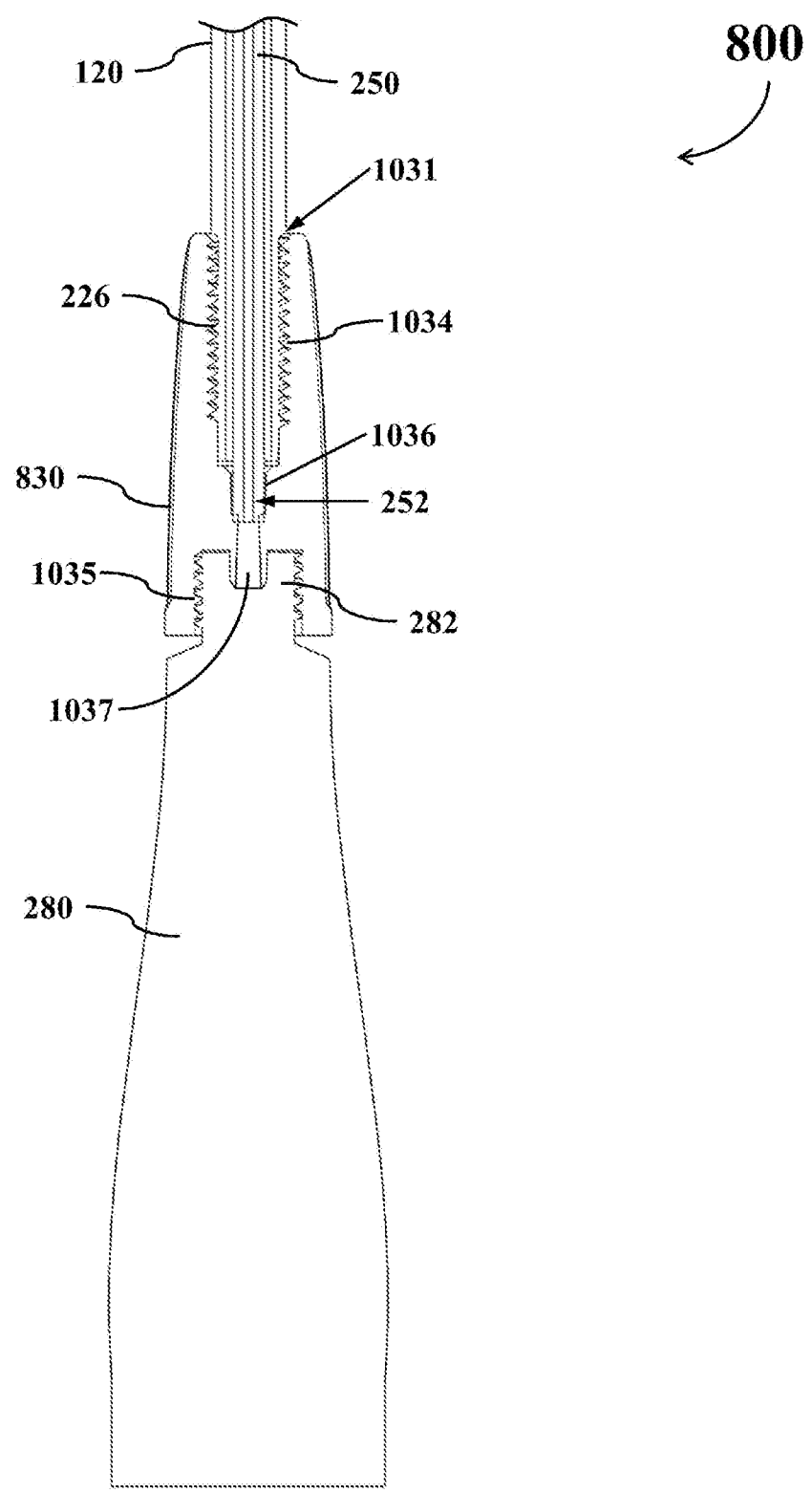
FIG. 11 shows a simplified cross-sectional diagram of a portion the adhesive deliver apparatus in FIG. 8.

FIG. 10 shows a simplified cross-sectional decomposed diagram of a portion of the adhesive deliver apparatus 800. FIG. 11 shows a simplified cross-sectional diagram of a portion of the adhesive deliver apparatus 800 when the support tube 120, the connector 830, the inner tube 250, and the adhesive tube 280 are assembled together.

As shown in FIG. 10, the connector 830 comprises a front opening 1031, a rear opening 1032, a hollow portion 1033, a second connection portion 1034, a third connection portion 1035, an inner tube socket 1036, and a hollow pillar 1037.

The front opening 1031 is positioned on the front end of the connector 830, and arranged to operably allow the support tube 120 and the inner tube 250 to insert into the connector 830 therethrough.

The rear opening 1032 is positioned on the rear end of the connector 830, and arranged to operably allow the nozzle 282 of the adhesive tube 280 to insert into the connector 830 therethrough.

The hollow portion 1033 is positioned inside the connector 830 for receiving the support tube 120 and the inner tube 250.

The second connection portion 1034 is formed on the inner surface of the connector 830, and arranged to operably engage with the first connection portion 226 of the support tube 120 so as to connect the support tube 120 with the connector 830.

The third connection portion 1035 is positioned in the rear end of the connector 830, and arranged to operably engage with the nozzle 282 so as to connect the nozzle 282 with the connector 830.

The inner tube socket 1036 is positioned inside the middle section of the connector 830, and arranged to operably engage with the inlet end 252 of the inner tube 250 so as to connect the inner tube 250 with the connector 830.

The hollow pillar 1037 is extended from the inner tube socket 1036 toward the rear end of the connector 830.

As shown in FIG. 11, when the nozzle 282 of the adhesive tube 280 is connected to the third connection portion 1035, the hollow pillar 1037 breaks through the nozzle seal 384 on the nozzle 282 and inserts into the nozzle 282.

As a result, a fluid transmission channel from the aperture of the hollow pillar 1037 to the tip element 840 can be established through connector 830 and the inner tube 250.

In practice, the second connection portion 1034 may be realized with complementary threaded elements, clamping elements, sleeves, or other suitable engaging elements capable of detachably connecting or permanently fixing the first connection portion 226 of the support tube 120 to the connector 830. The third connection portion 1035 may be realized with appropriately dimensioned threaded elements, clamping elements, sleeves, or other suitable engaging elements capable of detachably connecting or permanently connecting the adhesive tube 280 to the connector 830.

The foregoing descriptions regarding the implementations of other corresponding components in the embodiments of FIG. 1 through FIG. 7 are also applicable to this embodiment. For the sake of brevity, those descriptions will not be repeated here.

Since the adhesive tube 280 is made of deformable materials, the user can press the press region 816 of the separable holder 810 to extrude the adhesive fluid out of the adhesive tube 280 and apply the extruded adhesive fluid to the target area. When the press region 816 of the separable holder 810 is pressed by the user, the press region 816 is deformed to cause the interior surface of the press region 816 to press the adhesive tube 280. In this situation, the adhesive fluid will be squeezed out from the adhesive tube 280 and then be transmitted through the inner tube 250 from the inlet end 252 to the outlet end 254. The user is allowed to control the amount of adhesive outputted from the outlet end 254 of the inner tube 250 by manipulating the pressing force applied on the press region 816. As described previously, the adhesive fluid inside the inner tube 250 is to be outputted toward outside of the adhesive deliver apparatus 800 through the tip element 840.

Figure 12:
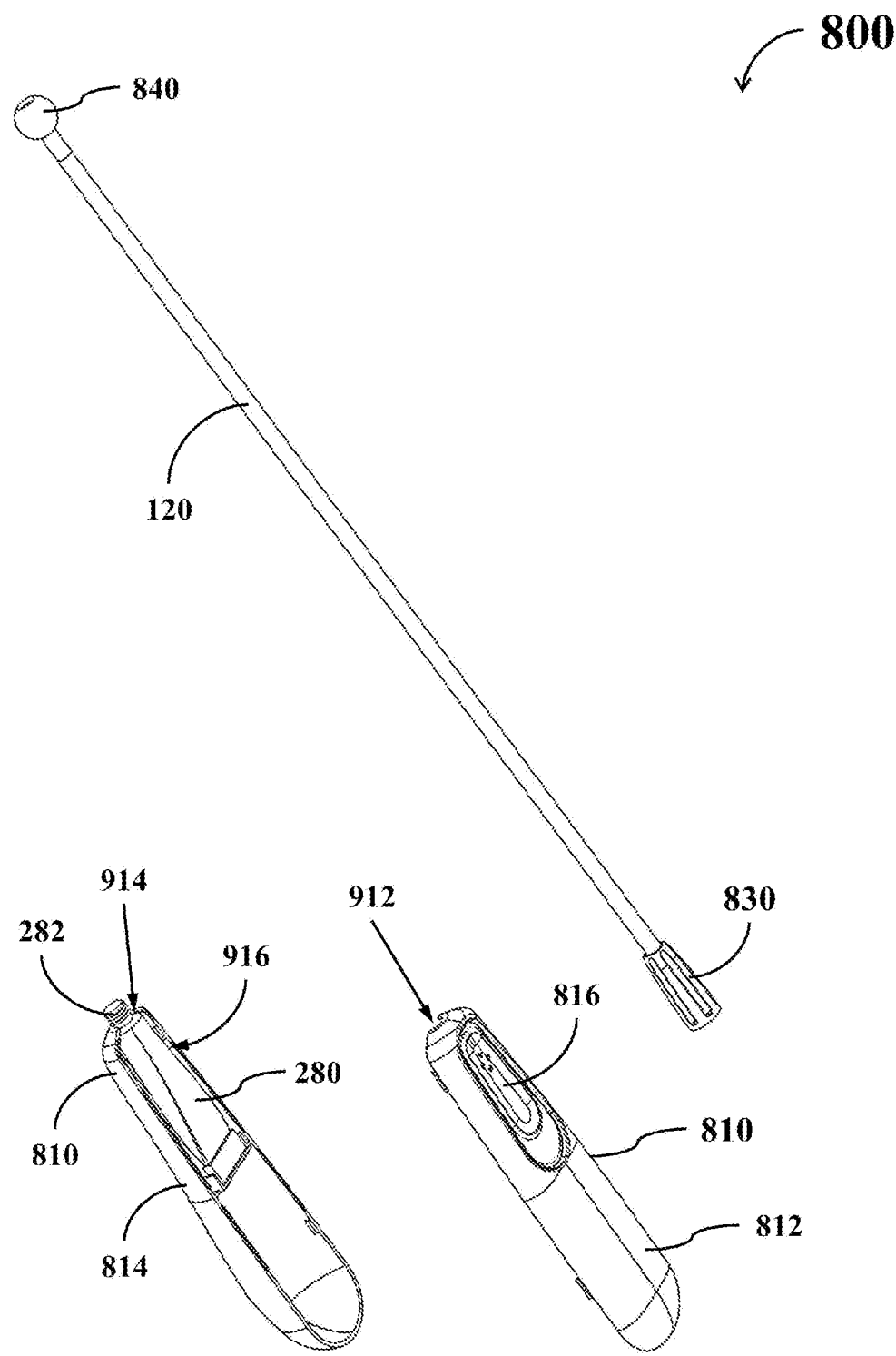
FIG. 12 shows a schematic decomposed diagram of the adhesive deliver apparatus in FIG. 8 when some parts thereof are assembled.
Figure 13:
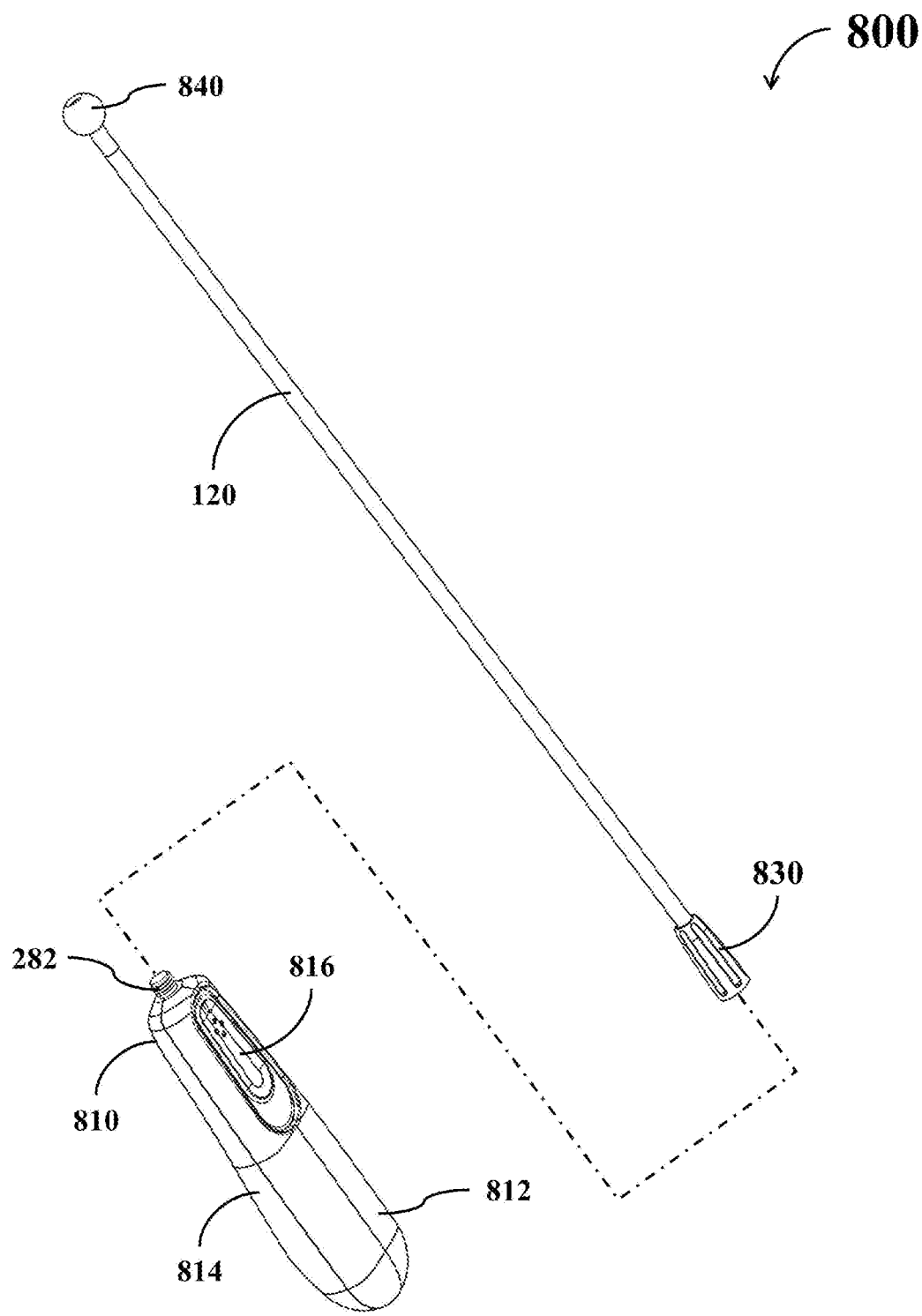
FIG. 13 shows a schematic decomposed diagram of the adhesive deliver apparatus in FIG. 8 when some parts thereof are assembled.

Please refer to FIG. 12 and FIG. 13, which show schematic decomposed diagrams of the adhesive deliver apparatus 800 when some parts thereof are assembled together.

Before the adhesive deliver apparatus 800 is used, the support tube 120, the connector 830, the tip element 840, and the inner tube 250 may be assembled together to form a first part of the adhesive deliver apparatus 800. On the other hand, a new adhesive tube 280 and the separable holder 810 may be assembled together to form a second part of the adhesive deliver apparatus 800.

As described previously, when the adhesive tube 280 is placed within the receiving chamber 916 inside the separable holder 810, the adhesive tube 280 is clamped by the first holder portion 812 and the second holder portion 814. In addition, the opening collectively formed by the first notch 912 and the second notch 914 allows only the nozzle 282 to pass therethrough, but does not allow the main body of the adhesive tube 280 to pass therethrough. Accordingly, the adhesive tube 280 can be secured within the separable holder 810 and will not depart from the separable holder 810 through the opening collectively formed by the first notch 912 and the second notch 914.

As shown in FIG. 13, when the user wants to use the adhesive deliver apparatus 800, the user may assemble the aforementioned first part and second part together to form a complete adhesive deliver apparatus 800. Specifically, the user may connect the connector 830 with the nozzle 282 of the adhesive tube 280 to render the hollow pillar 375 of the connector 830 to break through the nozzle seal 384 on the nozzle 282 and to insert into the nozzle 282.

After completing the assembling of the adhesive deliver apparatus 800, the user can manipulate the separable holder 810 to move the tip element 840 to a target area on which the adhesive fluid needs to be applied. The user can press the press region 816 of the separable holder 810 to squeeze the adhesive fluid out from the adhesive tube 280, so that the adhesive fluid contained in the adhesive tube 280 can enter into the inlet end 252 of the inner tube 250 and be transmitted to the outlet end 254 of the inner tube 250 through the inner tube 250. As described previously, the adhesive fluid inside the inner tube 250 will be outputted toward the target area through the tip element 840.

Afterwards, when the user stops pressing the press region 816 of the separable holder 810, the press region 816 will restore to its original position, and the shape of the deformable adhesive tube 280 will be slightly restored since the adhesive tube 280 is made by materials with some elasticity. In this situation, a small suction force will be generated within the fluid transmission channel and the adhesive tube 280 described above by the slight restoration of the shape of the adhesive tube 280. As a result, the adhesive fluid will be retained within the inner tube 250 and the tip element 840 to prevent the adhesive fluid from dripping when the user stops pressing the press region 816 of the separable holder 810.

In addition, by configuring the outlet aperture of the rounded outlet element 942 to have a rounded edge, the likelihood that residual adhesive blocks the outlet aperture of the tip element 840 can be effectively reduced.

In practice, each of the two terminals of the fastening element 944 may be designed to have a rounded corner to prevent the solidified adhesive to stick to either terminal of the fastening element 944. Similarly, the connection portion of the rounded outlet element 942 may be designed to have a rounded corner to prevent the solidified adhesive to stick to the connection portion of the rounded outlet element 942.

Figure 14:
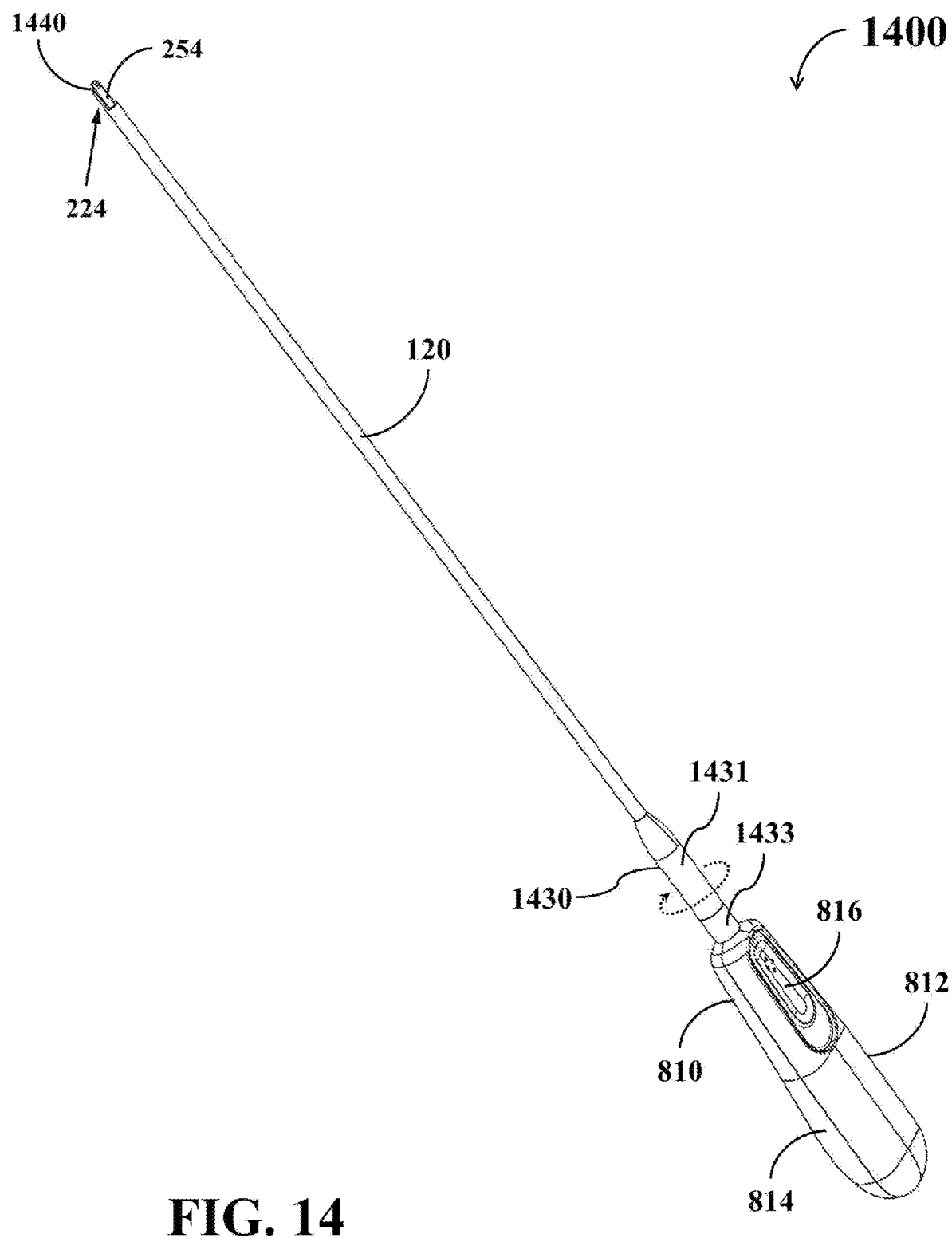
FIG. 14 shows a simplified schematic diagram of a hand-held adhesive deliver apparatus according to a third embodiment.
Figure 15:
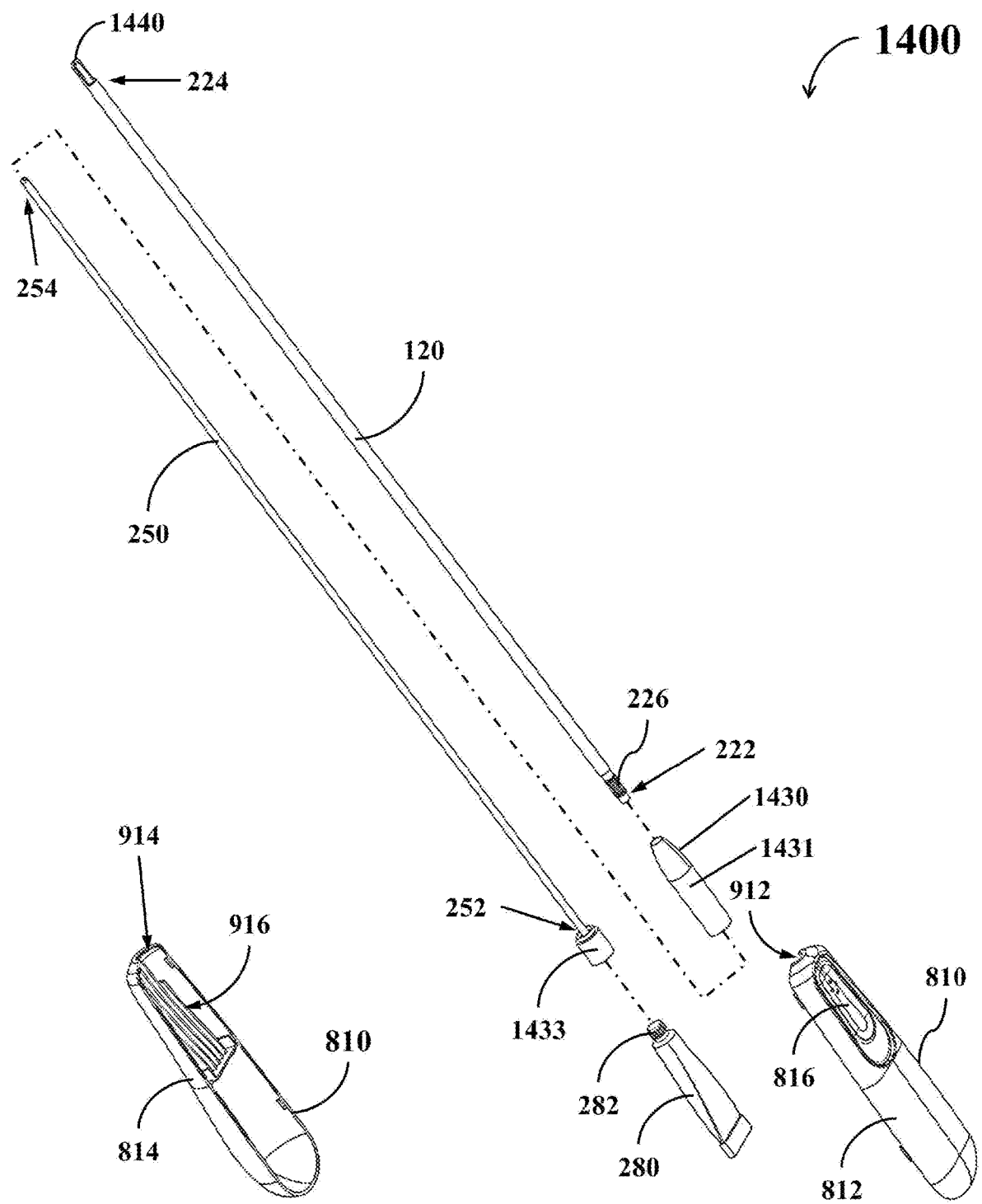
FIG. 15 shows a schematic decomposed diagram of the adhesive deliver apparatus in FIG. 14.

Please refer to FIG. 14 and FIG. 15. FIG. 14 shows a simplified schematic diagram of a hand-held adhesive deliver apparatus 1400 according to a third embodiment. FIG. 15 shows a schematic decomposed diagram of the adhesive deliver apparatus 1400. The adhesive deliver apparatus 1400 can also be utilized for delivering an adhesive fluid contained in the adhesive tube 280 to target areas of difficult access.

The embodiment of FIG. 14 and FIG. 15 is similar to the previous embodiments shown in FIG. 8 through FIG. 13, but the connector 830 and the tip element 840 in the embodiment of FIG. 8 through FIG. 13 are respectively replaced by a connector 1430 and a tip element 1440 in the embodiment of FIG. 14 and FIG. 15.

As shown in FIG. 14 and FIG. 15, the connector 1430 comprises a front-end element 1431 and a rear-end element 1433. The structure and functions of the connector 1430 will be further described in the following by reference to FIG. 16 and FIG. 17.

Figure 16:
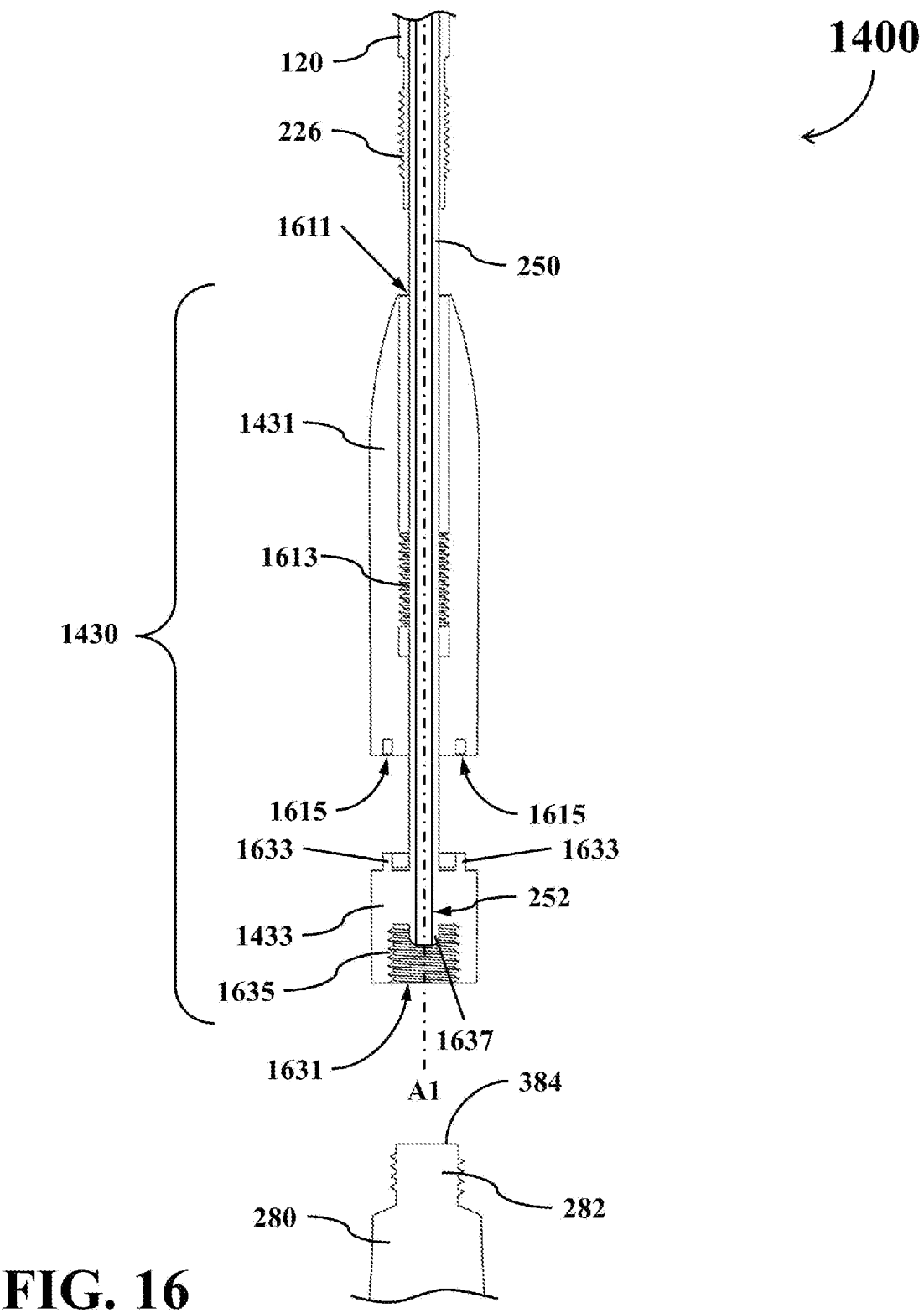
FIG. 16 shows a simplified cross-sectional decomposed diagram of a portion the adhesive deliver apparatus in FIG. 14.
Figure 17:
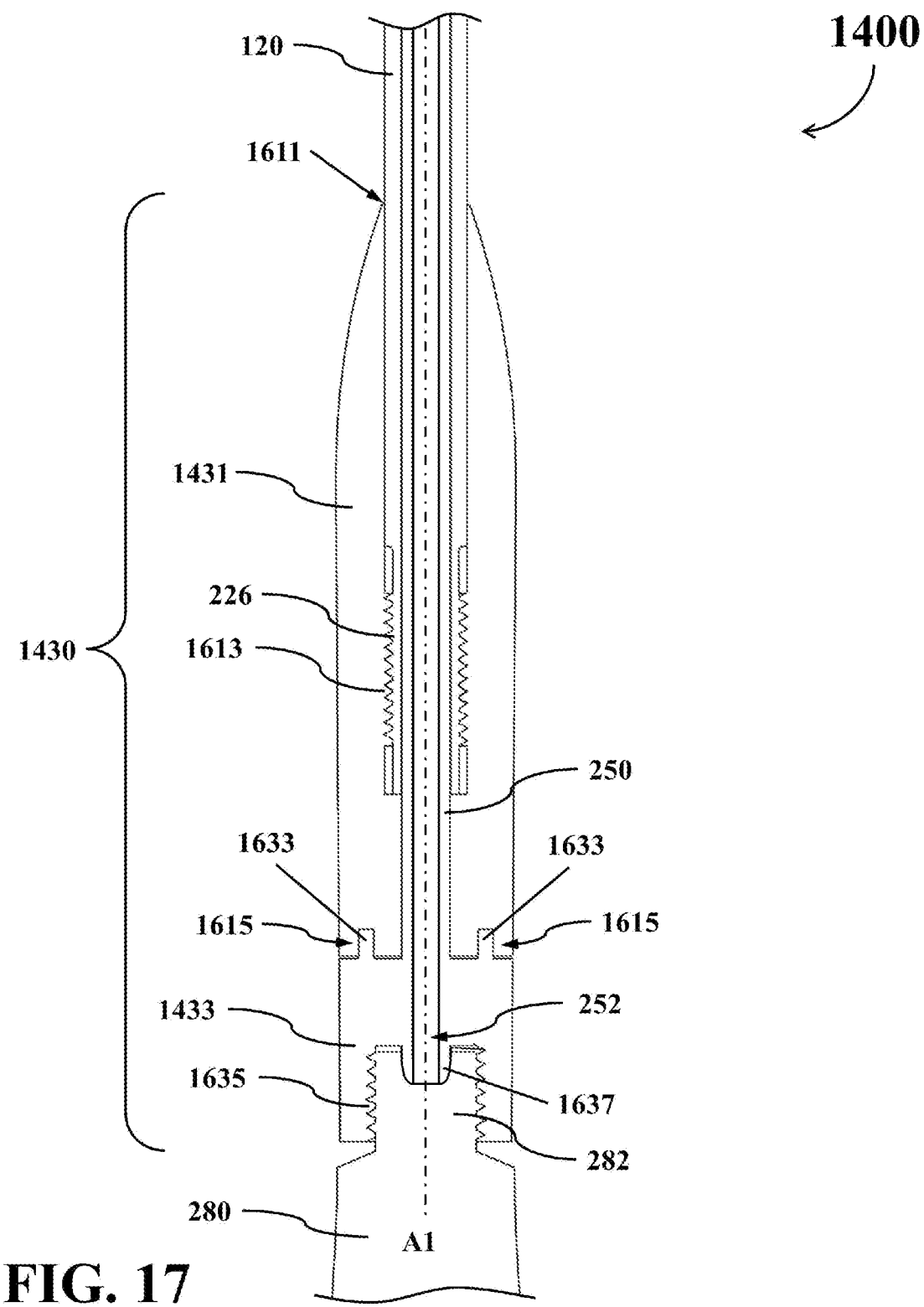
FIG. 17 shows a simplified cross-sectional diagram of a portion the adhesive deliver apparatus in FIG. 14.

FIG. 16 shows a simplified cross-sectional decomposed diagram of a portion of the adhesive deliver apparatus 1400. FIG. 17 shows a simplified cross-sectional diagram of a portion the adhesive deliver apparatus 1400 when the support tube 120, the connector 1430, the inner tube 250, and the adhesive tube 280 are assembled together.

The front-end element 1431 is utilized for connecting with the support tube 120. As shown in FIG. 16, the front-end element 1431 comprises a hollow front opening 1611, a second connection portion 1613, and a third connection portion 1615.

The front opening 1611 is positioned on the front end of the front-end element 1431, and arranged to operably allow the support tube 120 and the inner tube 250 to insert into the front-end element 1431 therethrough. The second connection portion 1613 is formed on the inner surface of the front-end element 1431, and arranged to operably engage with the first connection portion 226 of the support tube 120 so as to connect the support tube 120 with the front-end element 1431. The third connection portion 1615 is positioned and formed on the rear end of the front-end element 1431.

The rear-end element 1433 is utilized for connecting with the front-end element 1431, the inner tube 250, and the adhesive tube 280. The rear-end element 1433 comprises a rear opening 1631, a fourth connection portion 1633, a fifth connection portion 1635, and a hollow pillar 1637.

The rear opening 1631 is positioned on the rear end of the rear-end element 1433, and arranged to operably allow the nozzle 282 of the adhesive tube 280 to insert into the rear-end element 1433 therethrough. The fourth connection portion 1633 is positioned in the front end of the rear-end element 1433, and arranged to operably engage with the third connection portion 1615 so as to connect the rear-end element 1433 with the front-end element 1431 while allow the front-end element 1431 to be rotated around a longitudinal axis A1 of the support tube 120. The fifth connection portion 1635 is positioned in the rear end of the rear-end element 1433, and arranged to operably engage with the nozzle 282 so as to connect the nozzle 282 with the rear-end element 1433. The hollow pillar 1637 is extended from the fifth connection portion 1635 toward the rear end of the rear-end element 1433.

In practice, the fourth connection portion 1633 and the third connection portion 1615 may be realized with complementary sleeves or other suitable engaging elements capable of detachably connecting the front-end element 1431 to the rear-end element 1433, while allowing the front-end element 1431 can be rotated around the longitudinal axis A1. For example, in the embodiment of FIGS. 16 and 17, the third connection portion 1615 may be realized with a circular-shaped groove formed on the rear end of the front-end element 1431, while the fourth connection portion 1633 may be realized with a ring-shaped structure protruded outward from the front surface of the rear-end element 1433.

In this embodiment, the inner tube 250 is integrated with the rear-end element 1433 of the connector 1430 to form a one-piece structure. Accordingly, the inlet end 252 of the inner tube 250 is also embedded within the rear-end element 1433, and the hollow pillar 1637 may be regarded as a part of the inlet end 252 of the inner tube 250.

As shown in FIG. 17, when the above parts of the connector 1430 are assembled with the support tube 120 and the adhesive tube 280, the front-end element 1431 is connected with the rear-end element 1433 through the engagement between the third connection portion 1615 and the fourth connection portion 1633, but the front-end element 1431 is allowed to rotate around the longitudinal axis A1 on the front surface of the rear-end element 1433.

When the nozzle 282 of the adhesive tube 280 is inserted into the rear opening 1631 and connected to the fifth connection portion 1635, the hollow pillar 1637 would break through the nozzle seal 384 on the nozzle 282 and insert into the nozzle 282.

As a result, a fluid transmission channel from the aperture of the hollow pillar 1637 to the tip element 1440 can be established through the connector 1430 and the inner tube 250.

The foregoing descriptions regarding the implementations of other corresponding components in the embodiments of FIG. 8 through FIG. 13 are also applicable to this embodiment. For the sake of brevity, those descriptions will not be repeated here.

Similar with the previous embodiments, when the press region 816 of the separable holder 810 is pressed by the user, the adhesive fluid will be squeezed out from the adhesive tube 280 and then be transmitted through the inner tube 250 from the inlet end 252 to the outlet end 254. The user is allowed to control the amount of adhesive outputted from the outlet end 254 of the inner tube 250 by manipulating the pressing force applied on the press region 816. As described previously, the adhesive fluid inside the inner tube 250 will be dispensed outside of the adhesive deliver apparatus 1400 through the tip element 1440.

Figure 18:
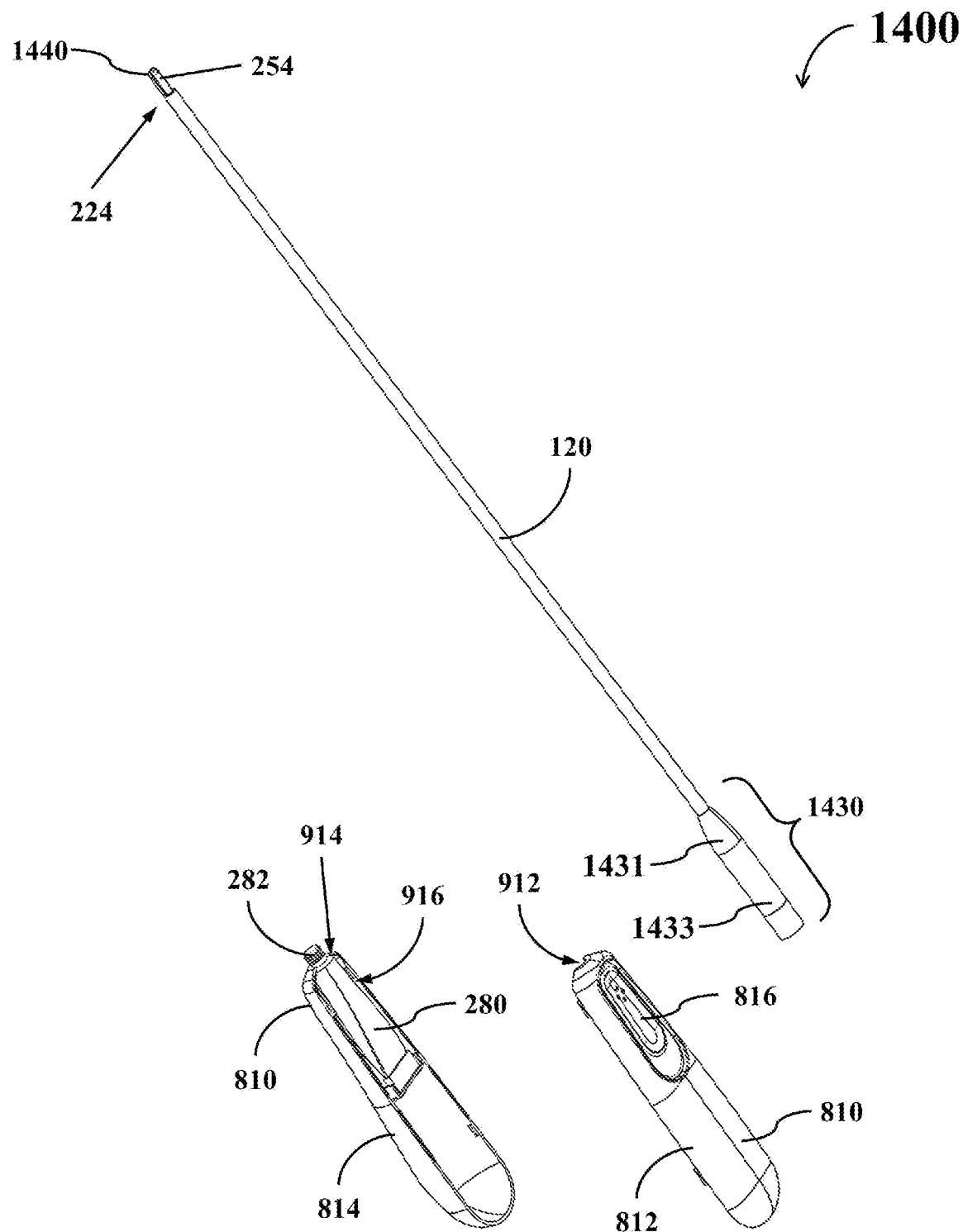
FIG. 18 shows a schematic decomposed diagram of the adhesive deliver apparatus in FIG. 14 when some parts thereof are assembled.
Figure 19:
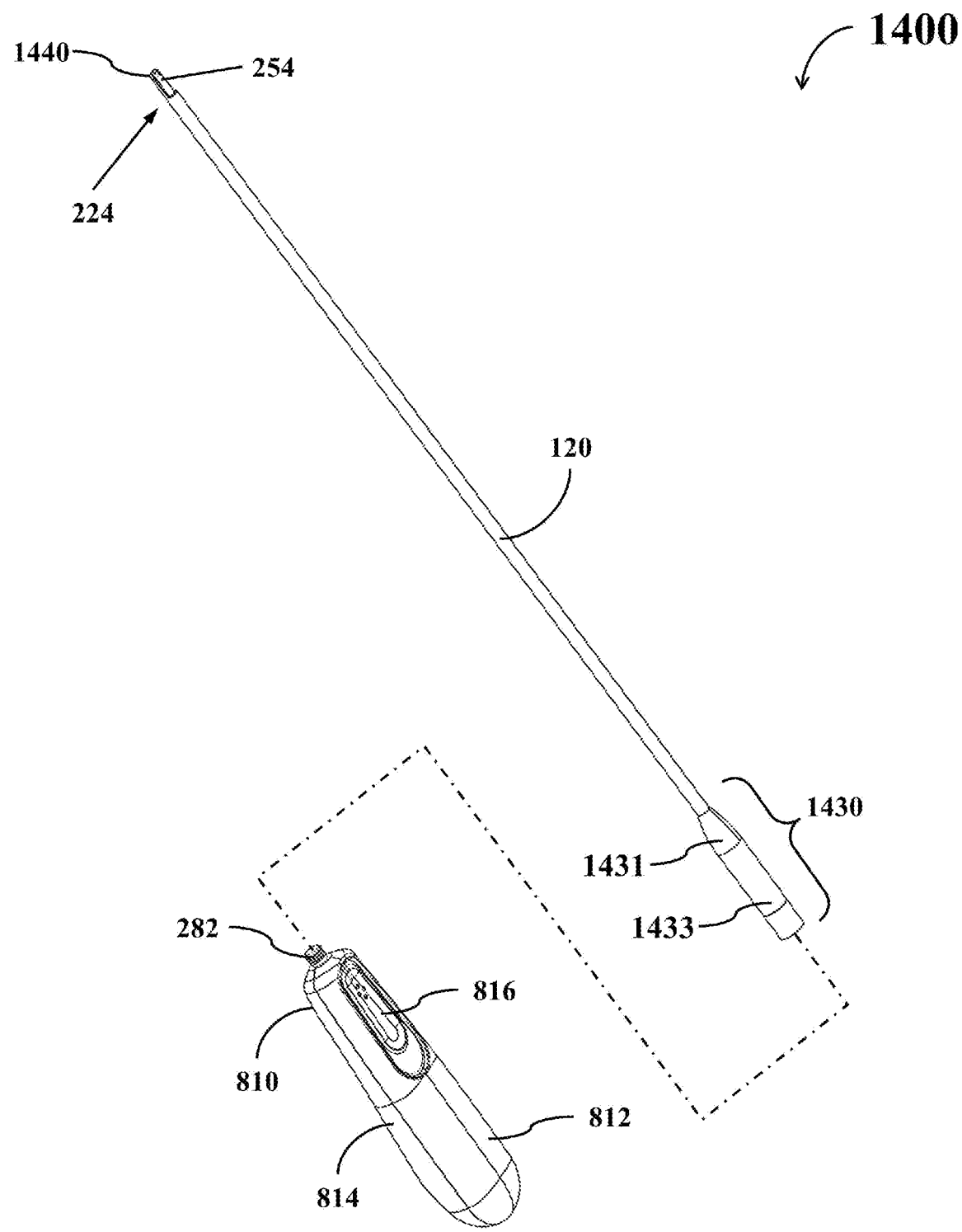
FIG. 19 shows a schematic decomposed diagram of the adhesive deliver apparatus in FIG. 14 when some parts thereof are assembled.

Please refer to FIG. 18 and FIG. 19, which show schematic decomposed diagrams of the adhesive deliver apparatus 1400 when some parts thereof are assembled together.

Before the adhesive deliver apparatus 1400 is used, the support tube 120, the connector 1430, the tip element 1440, and the inner tube 250 may be assembled together to form a first part of the adhesive deliver apparatus 1400. On the other hand, an adhesive tube 280 and the separable holder 810 may be assembled together to form a second part of the adhesive deliver apparatus 1400.

As described previously, when the adhesive tube 280 is placed within the receiving chamber 916 inside the separable holder 810, the adhesive tube 280 is clamped by the first holder portion 812 and the second holder portion 814. In addition, the opening collectively formed by the first notch 912 and the second notch 914 only allows the nozzle 282 to pass therethrough, but does not allow the main body of the adhesive tube 280 to pass therethrough. Accordingly, the adhesive tube 280 can be secured within the separable holder 810 and will not depart from the separable holder 810 through the opening collectively formed by the first notch 912 and the second notch 914.

As shown in FIG. 19, when the user wants to use the adhesive deliver apparatus 800, the user may assemble the aforementioned first part and second part together to form a complete adhesive deliver apparatus 1400. Specifically, the user may connect the connector 1430 with the nozzle 282 of the adhesive tube 280 to render the hollow pillar 1637 of the connector 1430 to break through the nozzle seal 384 on the nozzle 282 and to insert into the nozzle 282.

Figure 20:
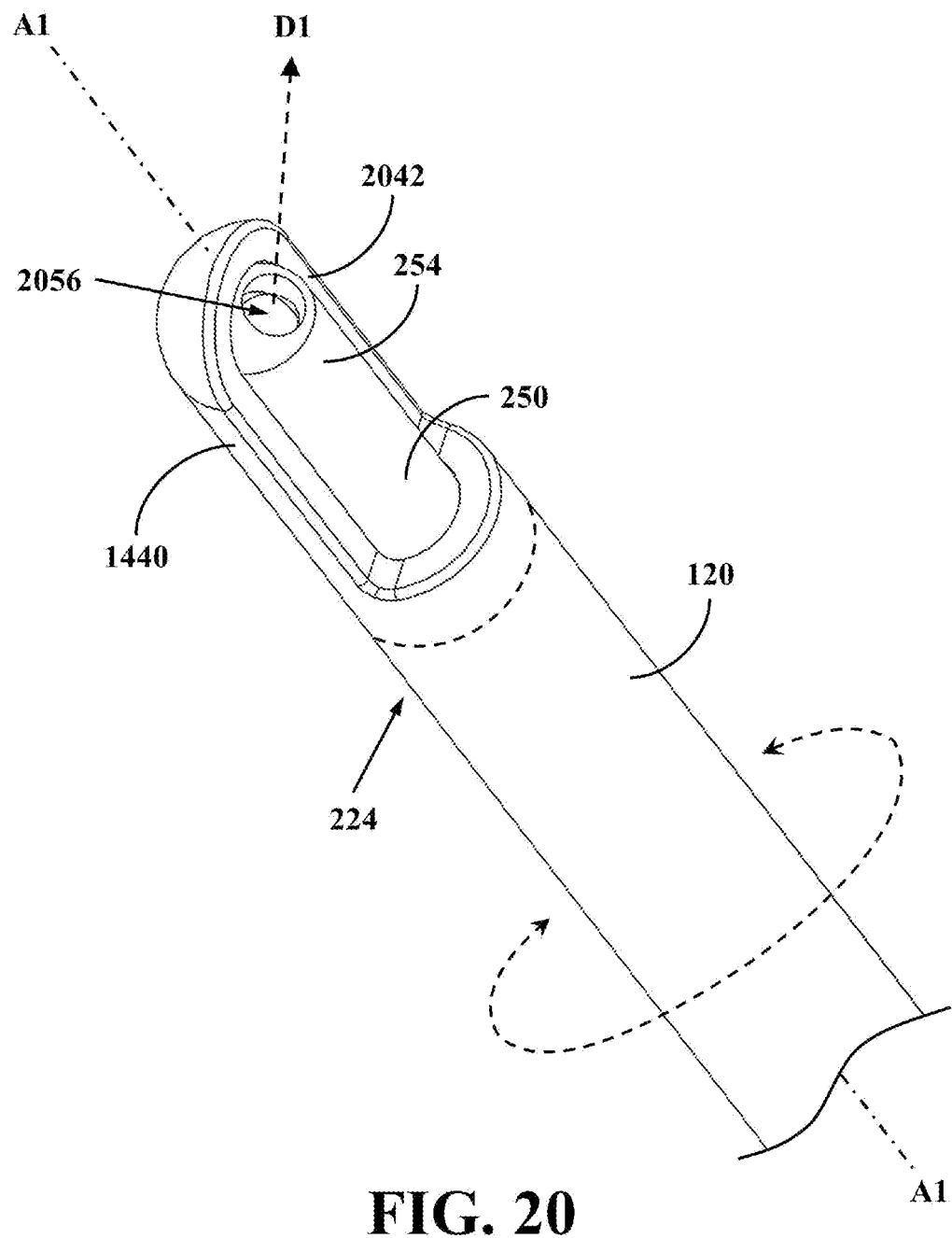
FIG. 20 is a schematic enlarged diagram of a partial area in FIG. 14 in accordance with an example embodiment.

Please refer to FIG. 20, which shows a schematic enlarged diagram of a portion of the adhesive deliver apparatus 1400 in accordance with an example embodiment.

As shown in FIG. 20, the tip element 1440 is positioned at the distal end 224 of the support tube 120. In practice, the tip element 1440 may be firmly connected to the distal end 224 of the support tube 120, or may be integrally formed together with the distal end 224 of the support tube 120.

The tip element 1440 comprises a shaving portion 2042, which covers only a portion of the outer surface of the outlet end 254 of the inner tube 250. As shown in FIG. 20, the outlet end 254 of the inner tube 250 has an aperture 2056 for outputting the adhesive fluid. In this embodiment, the aperture 2056 of the outlet end 254 is oriented to an output direction, D1, which is not parallel with the longitudinal axis A1 of the support tube 120.

When the support tube 120 is rotated around the longitudinal axis A1, the shaving portion 2042 would also rotate around the longitudinal axis A1 to shave the aperture 2056 and its adjacent area, and thereby removing any residual adhesive accumulated on the aperture 2056.

After completing the assembling of the adhesive deliver apparatus 1400, the user can manipulate the separable holder 810 to move the tip element 1440 to a target area on which the adhesive fluid needs to be applied. The user can press the press region 816 of the separable holder 810 to squeeze the adhesive fluid out from the adhesive tube 280, so that the adhesive fluid contained in the adhesive tube 280 can enter into the inlet end 252 of the inner tube 250 and be transmitted to the outlet end 254 of the inner tube 250 through the inner tube 250. As described previously, the adhesive fluid inside the inner tube 250 will be outputted toward the target area from the aperture 2056.

Afterwards, when the user stops pressing the press region 816 of the separable holder 810, the elasticity of the press region 816 will restore the press region 816 to its original position, and the shape of the deformable adhesive tube 280 will be slightly restored since the adhesive tube 280 is made by materials with some elasticity. In this situation, a small suction force will be generated within the fluid transmission channel and the adhesive tube 280. As a result, the adhesive fluid will be retained within the inner tube 250 to prevent the adhesive fluid from dripping when the user stops pressing the press region 816 of the separable holder 810.

After the adhesive deliver apparatus 1400 is used to apply the adhesive on the target area, residual adhesive may accumulate on the aperture 2056, thereby blocking the aperture 2056 from dispensing adhesive. As a consequence, the user may rotate the front-end element 1431 of the connector 1430 around the longitudinal axis A1, so as to rotate the tip element 1440. In this way, the shaving portion 2042 of the tip element 1440 would shave the aperture 2056 of the inner tube 250 and its adjacent area to remove residual adhesive accumulated on the aperture 2056, thereby preventing the aperture 2056 from being blocked by the residual adhesive.

The adhesive deliver apparatuses 100, 800, and 1400 disclosed above may be used to fulfill the needs of different applications, such as binding objects, closing wounds, fixing meshes inside human or animal body during the surgical treatment.

For example, the disclosed adhesive deliver apparatuses 100, 800, and 1400 may be utilized for fixing meshes or tissue in hernia repair surgery. In this case, the user can use the disclosed adhesive deliver apparatus 100, 800, or 1400 to apply the adhesive fluid to areas between the mesh and the biological tissue.

Please note that the structure of the adhesive deliver apparatuses 100, 800, and 1400 disclosed above are merely exemplary embodiments, rather than restrictions to practical implementations.

For example, in some embodiments where backflow of the adhesive is not a concern, the backflow prevention valve 235 in the aforementioned adhesive deliver apparatus 100 may be omitted.

In some embodiments where leakage of the adhesive fluid is not a concern or can be resolved by other solutions, the leakproof ring 233, the leakproof ring 260, and/or the leakproof ring 270 in the aforementioned adhesive deliver apparatus 100 may be omitted.

In addition, the aforementioned connectors 130, 830, and 1430 may be exchangeable between different embodiments. For example, the connector 1430 may be used in the adhesive deliver apparatus 800.

Similarly, the aforementioned tip elements 140, 840, and 1440 may be exchangeable between different embodiments. For example, the tip element 840 may be used in the adhesive deliver apparatus 100. For another example, the tip element 140 may be used in the adhesive deliver apparatus 800.

Furthermore, the support tube 120 may be designed to have a slightly bended shape at the distal end 224, so as to change the output direction of the adhesive fluid.

It can be appreciated from the foregoing descriptions that each of the disclosed adhesive deliver apparatuses 100, 800, and 1400 has an elongated delivery tube, so that they can be utilized for delivering the adhesive fluid contained in the deformable adhesive tube 280 to the areas where conventional adhesive dispenser cannot reach or access.

In addition, the nozzle seal 384 on the nozzle 282 of the adhesive tube 280 can be easily penetrated by the hollow pillar in the disclosed connector 130, 830, or 1430. Therefore, the disclosed adhesive deliver apparatuses 100, 800, and 1400 require no complex mechanical part to open the adhesive tube 280.

Furthermore, since the adhesive tube 280 is made by non-frangible materials and would not result in fragments when it is opened, no complex mechanical parts for filtering fragments of the adhesive tube 280 is required.

Accordingly, the disclosed adhesive deliver apparatuses 100, 800, and 1400 have much simpler structure than the conventional solution, and thus effectively reduce the complexity in manufacturing and assembling.

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The term "couple" is intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

The term "and/or" may comprise any and all combinations of one or more of the associated listed items. In addition, the singular forms "a," "an," and "the" herein are intended to comprise the plural forms as well, unless the context clearly indicates otherwise.

Throughout the description and claims, the term "element" contains the concept of component, layer, or region.

In the drawings, the size and relative sizes of some elements may be exaggerated or simplified for clarity. Accordingly, unless the context clearly specifies, the shape, size, relative size, and relative position of each element in the drawings are illustrated merely for clarity, and not intended to be used to restrict the claim scope.

For the purpose of explanatory convenience in the specification, spatially relative terms, such as "on," "above," "below," "beneath," "higher," "lower," "upward," "downward," and the like, may be used herein to describe the function of a particular element or to describe the relationship of one element to another element(s) as illustrated in the drawings. It will be understood that the spatially relative terms are intended to encompass different orientations of the element in use, in operations, or in assembly in addition to the orientation depicted in the drawings. For example, if the element in the drawings is turned over, elements described as "on" or "above" other elements would then be oriented "under" or "beneath" the other elements. Thus, the exemplary term "beneath" can encompass both an orientation of above and beneath.

Throughout the description and claims, it will be understood that when a component is referred to as being "positioned on," "positioned above," "connected to," "engaged with," or "coupled with" another component, it can be directly on, directly connected to, or directly engaged with the other component, or intervening component may be present. In contrast, when a component is referred to as being "directly on," "directly connected to," or "directly engaged with" another component, there are no intervening components present.

Other embodiments of the invention will be apparent to those skilled in the art from consideration of the specification and practice of the invention disclosed herein. It is intended that the specification and examples be considered as exemplary only, with a true scope and spirit of the invention indicated by the following claims.

What is claimed is:

1. An adhesive delivery apparatus (100; 800; 1400) for delivering an adhesive fluid contained in an adhesive tube (280) to a target area, the adhesive delivery apparatus (100; 800; 1400) comprising:
    a separable holder (110; 810) having a flexible press region (116; 816) thereon and comprising an interior receiving chamber (216; 916; 1416) for placing the adhesive tube (280);
    a support tube (120) having a substantially elongated shape and comprising a proximal end (222), a distal end (224), and a first connection portion (226), wherein the first connection portion (226) is positioned on an outer surface of the support tube (120) and approximating to the proximal end (222);

a connector (130; 830; 1430) connected with the proximal end (222) of the support tube (120) and arranged to operably connect with a nozzle (282) of the adhesive tube (280);
an inner tube (250) positioned within the support tube (120) and comprising an inlet end (252) connected with the connector (130; 830; 1430) and an outlet end (254) approximating to the distal end (224) of the support tube (120); and
a hollow tip element (140; 840; 1440) positioned at the distal end (224) of the support tube (120) and arranged to operably fasten the outlet end (254) of the inner tube (250) at the distal end (224) of the support tube (120);
wherein when the press region (116; 816) is pressed to cause an interior surface of the press region (116; 816) to press the adhesive tube (280), the adhesive fluid will be squeezed out from the adhesive tube (280) and transmitted through the inner tube (250) from the inlet end (252) to the outlet end (254);
wherein the connector (130) comprises:
a front-end element (231) comprising:
  a front opening (311) allowing the support tube (120) and the inner tube (250) to insert into the front-end element (231) therethrough;
  a hollow portion (312) positioned inside the front-end element (231);
  a second connection portion (313) formed on an inner surface of the front-end element (231), and arranged to operably engage with the first connection portion (226) of the support tube (120) so as to connect the support tube (120) with the front-end element (231);
  a third connection portion (314) formed on an outer surface of the front-end element (231); and
  a first chamber (315) formed in a rear end of the front-end element (231); and
a rear-end element (237) comprising:
  a rear opening (371) allowing the nozzle (282) of the adhesive tube (280) to insert into the rear-end element (237) therethrough;
  a fourth connection portion (372) positioned in a front end of the rear-end element (237), and arranged to operably engage with the third connection portion (314) so as to connect the rear-end element (237) with the front-end element (231);
  a fifth connection portion (373) arranged to operably engage with the nozzle (282) so as to connect the nozzle (282) with the rear-end element (237);
  a second chamber (374) formed within the rear-end element (237) and arranged to operably receive the rear end of the front-end element (231); and
  a hollow pillar (375) extended from the second chamber (374) toward a rear end of the rear-end element (237), wherein when the nozzle (282) of the adhesive tube (280) is connected to the fifth connection portion (373), the hollow pillar (375) breaks through a nozzle seal (384) on the nozzle (282) and inserts into the nozzle (282).

2. The adhesive delivery apparatus (100; 800; 1400) of claim 1, wherein the connector (130) further comprises: a backflow prevention valve (235) positioned within the first chamber (315) of the front-end element (231), wherein the backflow prevention valve (235) comprises: a duck-bill portion (352) positioned on a front end of the backflow prevention valve (235), and arranged to operably prevent backflow from the front-end element (231); and a flange (354) formed on a rear end of the backflow prevention valve (235) and arranged to operably limit a position between the front-end element (231) and the backflow prevention valve (235).

3. The adhesive delivery apparatus (100; 800; 1400) of claim 1, wherein the tip element (140) is inserted into the distal end (224) of the support tube (120), the outlet end (254) of the inner tube (250) is inserted into the tip element (140), and the adhesive fluid inside the inner tube (250) is to be outputted toward outside of the adhesive delivery apparatus (100; 800; 1400) through the tip element (140).

4. The adhesive delivery apparatus (100; 800; 1400) of claim 1, wherein the tip element (840) comprises: a rounded outlet element (942) positioned at the distal end (224) of the support tube (120) and having an outlet aperture with a rounded edge; and a fastening element (944) connected between the rounded outlet element (942) and the distal end (224) of the support tube (120); wherein the adhesive fluid inside the inner tube (250) is to be outputted toward outside of the adhesive delivery apparatus (100; 800; 1400) through the fastening element (944) and the rounded outlet element (942).

5. The adhesive delivery apparatus (100; 800; 1400) of claim 1, wherein the tip element (1440) comprises: a shaving portion (2042) positioned at the distal end (224) of the support tube (120) and covering only a portion of an outer surface of the outlet end (254) of the inner tube (250); wherein an aperture (2056) in the outlet end (254) of the inner tube (250) is oriented to an output direction (D1) which is not parallel with a longitudinal axis (A1) of the support tube (120), and when the support tube (120) is rotated around the longitudinal axis (A1), the shaving portion (2042) shaves the aperture (2056) and adjacent area so as to remove residual adhesive on the aperture (2056).

6. The adhesive delivery apparatus (100; 800; 1400) of claim 1, wherein the separable holder (110) comprises: a limiting notch (218) positioned beside the receiving chamber (216) inside the separable holder (110), and arranged to operably allow the nozzle (282) of the adhesive tube (280) to pass therethrough, but not allow a main body of the adhesive tube (280) to pass therethrough, so as to prevent the adhesive tube (280) from departing from the separable holder (110).

7. The adhesive delivery apparatus (100; 800; 1400) of claim 6, wherein the separable holder (110) further comprises: an opening (118) positioned beside the limiting notch (218), arranged to operably allow a user to observe the engagement between the nozzle (282) and the connector (130).

8. The adhesive delivery apparatus (100; 800; 1400) of claim 1, wherein the separable holder (810) comprises: a first notch (912) and a second notch (914) positioned in a front end of the separable holder (810), and arranged to collectively form an opening allowing the nozzle (282) of the adhesive tube (280) to pass therethrough, but not allowing a main body of the adhesive tube (280) to pass therethrough, so as to prevent the adhesive tube (280) from departing from the separable holder (810).

9. The adhesive delivery apparatus (100; 800; 1400) of claim 1, wherein the tip element (140) comprises: an outer surface (542) arranged to operably engage with an inner surface of the support tube (120) to connect the tip element (140) with the support tube (120); a connecting hole (544) arranged to operably allow the outlet end (254) of the inner tube (250) to be inserted into the tip element (140) therethrough; and an inner surface (546) arranged to operably engage with an outer surface of the inner tube (250) to connect the tip element (140) with the inner tube (250);

wherein the connecting hole (544) has a cross-section of a non-round shape, and one or more air channels are formed between the tip element (140) and the inner tube (250) when the outlet end (254) of the inner tube (250) is inserted into the connecting hole (544).

10. An adhesive delivery apparatus (100; 800; 1400) for delivering an adhesive fluid contained in an adhesive tube (280) to a target area, the adhesive delivery apparatus (100; 800; 1400) comprising:

a separable holder (110; 810) having a flexible press region (116; 816) thereon and comprising an interior receiving chamber (216; 916; 1416) for placing the adhesive tube (280);

a support tube (120) having a substantially elongated shape and comprising a proximal end (222), a distal end (224), and a first connection portion (226), wherein the first connection portion (226) is positioned on an outer surface of the support tube (120) and approximating to the proximal end (222);

a connector (130; 830; 1430) connected with the proximal end (222) of the support tube (120) and arranged to operably connect with a nozzle (282) of the adhesive tube (280);

an inner tube (250) positioned within the support tube (120) and comprising an inlet end (252) connected with the connector (130; 830; 1430) and an outlet end (254) approximating to the distal end (224) of the support tube (120); and a hollow tip element (140; 840; 1440) positioned at the distal end (224) of the support tube (120) and arranged to operably fasten the outlet end (254) of the inner tube (250) at the distal end (224) of the support tube (120);

wherein when the press region (116; 816) is pressed to cause an interior surface of the press region (116; 816) to press the adhesive tube (280), the adhesive fluid will be squeezed out from the adhesive tube (280) and transmitted through the inner tube (250) from the inlet end (252) to the outlet end (254);

wherein the connector (830) comprises:

a front opening (1031) allowing the support tube (120) and the inner tube (250) to insert into the connector (830) therethrough;

a rear opening (1032) allowing the nozzle (282) of the adhesive tube (280) to insert into the connector (830) therethrough;

a hollow portion (1033) positioned inside the connector (830);

a second connection portion (1034) formed on an inner surface of the connector (830), and arranged to operably engage with the first connection portion (226) of the support tube (120) so as to connect the support tube (120) with the connector (830);

a third connection portion (1035) arranged to operably engage with the nozzle (282) so as to connect the nozzle (282) with the connector (830);

an inner tube socket (1036) arranged to operably engage with the inlet end (252) of the inner tube (250) so as to connect the inner tube (250) with the connector (830); and a hollow pillar (1037) extended from the inner tube socket (1036) toward a rear end of the connector (830), wherein when the nozzle (282) of the adhesive tube (280) is connected to the fifth connection portion (373), the hollow pillar (375) breaks through a nozzle seal (384) on the nozzle (282) and inserts into the nozzle (282).

11. The adhesive delivery apparatus (100; 800; 1400) of claim 10, wherein the tip element (140) is inserted into the distal end (224) of the support tube (120), the outlet end (254) of the inner tube (250) is inserted into the tip element (140), and the adhesive fluid inside the inner tube (250) is to be outputted toward outside of the adhesive delivery apparatus (100; 800; 1400) through the tip element (140).

12. The adhesive delivery apparatus (100; 800; 1400) of claim 10, wherein the tip element (840) comprises: a rounded outlet element (942) positioned at the distal end (224) of the support tube (120) and having an outlet aperture with a rounded edge; and a fastening element (944) connected between the rounded outlet element (942) and the distal end (224) of the support tube (120); wherein the adhesive fluid inside the inner tube (250) is to be outputted toward outside of the adhesive delivery apparatus (100; 800; 1400) through the fastening element (944) and the rounded outlet element (942).

13. The adhesive delivery apparatus (100; 800; 1400) of claim 10, wherein the tip element (1440) comprises: a shaving portion (2042) positioned at the distal end (224) of the support tube (120) and surrounding only a portion of an outer surface of the outlet end (254) of the inner tube (250); wherein an aperture (2056) in the outlet end (254) of the inner tube (250) is oriented to an output direction (D1) which is not parallel with a longitudinal axis (A1) of the support tube (120), and when the support tube (120) is rotated around the longitudinal axis (Al), the shaving portion (2042) shaves the aperture (2056) and related neighboring regions so as to remove residual adhesive on the aperture (2056).

14. An adhesive delivery apparatus (100; 800; 1400) for delivering an adhesive fluid contained in an adhesive tube (280) to a target area, the adhesive delivery apparatus (100; 800; 1400) comprising:

a separable holder (110; 810) having a flexible press region (116; 816) thereon and comprising an interior receiving chamber (216; 916; 1416) for placing the adhesive tube (280);

a support tube (120) having a substantially elongated shape and comprising a proximal end (222), a distal end (224), and a first connection portion (226), wherein the first connection portion (226) is positioned on an outer surface of the support tube (120) and approximating to the proximal end (222);

a connector (130; 830; 1430) connected with the proximal end (222) of the support tube (120) and arranged to operably connect with a nozzle (282) of the adhesive tube (280);

an inner tube (250) positioned within the support tube (120) and comprising an inlet end (252) connected with the connector (130; 830; 1430) and an outlet end (254) approximating to the distal end (224) of the support tube (120); and a hollow tip element (140; 840; 1440) positioned at the distal end (224) of the support tube (120) and arranged to operably fasten the outlet end (254) of the inner tube (250) at the distal end (224) of the support tube (120);

wherein when the press region (116; 816) is pressed to cause an interior surface of the press region (116; 816) to press the adhesive tube (280), the adhesive fluid will be squeezed out from the adhesive tube (280) and transmitted through the inner tube (250) from the inlet end (252) to the outlet end (254);

wherein the connector (1430) comprises:

a front-end element (1431) comprising:

a front opening (1611) allowing the support tube (120) and the inner tube (250) to insert into the front-end element (1431) therethrough;

a second connection portion (1613) formed on an inner surface of the front-end element (1431), and arranged to operably engage with the first connection portion (226) of the support tube (120) so as to connect the support tube (120) with the front-end element (1431);

a third connection portion (1615) formed on a rear side of the front-end element (1431);

a rear-end element (1433) connected with the inner tube (250) and penetrated by the inner tube (250), the rear-end element (1433) comprising:

a rear opening (1631) allowing the nozzle (282) of the adhesive tube (280) to insert into the rear-end element (1433) therethrough;

a fourth connection portion (1633) formed on a front side of the rear-end element (1433), and arranged to operably engage with the third connection portion (1615) so as to connect the rear-end element (1433) with the front-end element (1431) while allow the front-end element (1431) to be rotated around a longitudinal axis (Al);

a fifth connection portion (1635) arranged to operably engage with the nozzle (282) so as to connect the nozzle (282) with the rear-end element (1433);

a hollow pillar (1637) extended from the inlet end (252) of the inner tube (250) toward a rear end of the rear-end element (1433), wherein when the nozzle (282) of the adhesive tube (280) is connected to the fifth connection portion (1635), the hollow pillar (1637) breaks through a nozzle seal (384) on the nozzle (282) and inserts into the nozzle (282).

15. The adhesive delivery apparatus (100; 800; 1400) of claim 14, wherein the tip element (140) is inserted into the distal end (224) of the support tube (120), the outlet end (254) of the inner tube (250) is inserted into the tip element (140), and the adhesive fluid inside the inner tube (250) is to be outputted toward outside of the adhesive delivery apparatus (100; 800; 1400) through the tip element (140).

16. The adhesive delivery apparatus (100; 800; 1400) of claim 14, wherein the tip element (840) comprises: a rounded outlet element (942) positioned at the distal end (224) of the support tube (120) and having an outlet aperture with a rounded edge; and a fastening element (944) connected between the rounded outlet element (942) and the distal end (224) of the support tube (120); wherein the adhesive fluid inside the inner tube (250) is to be outputted toward outside of the adhesive delivery apparatus (100; 800; 1400) through the fastening element (944) and the rounded outlet element (942).

17. The adhesive delivery apparatus (100; 800; 1400) of claim 14, wherein the tip element (1440) comprises: a shaving portion (2042) positioned at the distal end (224) of the support tube (120) and surrounding only a portion of an outer surface of the outlet end (254) of the inner tube (250); wherein an aperture (2056) in the outlet end (254) of the inner tube (250) is oriented to an output direction (D1) which is not parallel with the longitudinal axis (Al) of the support tube (120), and when the support tube (120) is rotated around the longitudinal axis (Al), the shaving portion (2042) shaves the aperture (2056) and related neighboring regions so as to remove residual adhesive on the aperture (2056).

18. An adhesive delivery apparatus (100; 800; 1400) for delivering an adhesive fluid contained in an adhesive tube (280) to a target area, the adhesive delivery apparatus (100; 800; 1400) comprising:

a support tube (120) comprising a proximal end (222) and a distal end (224);

a connector (130; 830; 1430) connected with the proximal end (222) of the support tube (120) and arranged to operably connect with a nozzle (282) of the adhesive tube (280);

an inner tube (250) positioned within the support tube (120) and comprising an inlet end (252) connected with the connector (130; 830; 1430) and an outlet end (254) approximating to the distal end (224) of the support tube (120); and a hollow tip element (140; 840; 1440) positioned at the distal end (224) of the support tube (120) and arranged to operably fasten the outlet end (254) of the inner tube (250) at the distal end (224) of the support tube (120);

wherein the adhesive fluid out from the adhesive tube (280) is transmitted through the inner tube (250) from the inlet end (252) to the outlet end (254);

wherein the connector (130) comprises:

a front-end element (231) comprising:

a front opening (311) allowing the support tube (120) and the inner tube (250) to insert into the front-end element (231) therethrough;

a hollow portion (312) positioned inside the front-end element (231);

a second connection portion (313) formed on an inner surface of the front-end element (231), and arranged to operably engage with the first connection portion (226) of the support tube (120) so as to connect the support tube (120) with the front-end element (231);

a third connection portion (314) formed on an outer surface of the front-end element (231); and a first chamber (315) formed in a rear end of the front-end element (231); and a rear-end element (237) comprising:

a rear opening (371) allowing the nozzle (282) of the adhesive tube (280) to insert into the rear-end element (237) therethrough;

a fourth connection portion (372) positioned in a front end of the rear-end element (237), and arranged to operably engage with the third connection portion (314) so as to connect the rear-end element (237) with the front-end element (231);

a fifth connection portion (373) arranged to operably engage with the nozzle (282) so as to connect the nozzle (282) with the rear-end element (237);

a second chamber (374) formed within the rear-end element (237) and arranged to operably receive the rear end of the front-end element (231); and a hollow pillar (375) extended from the second chamber (374) toward a rear end of the rear-end element (237), wherein when the nozzle (282) of the adhesive tube (280) is connected to the fifth connection portion (373), the hollow pillar (375) breaks through a nozzle seal (384) on the nozzle (282) and inserts into the nozzle (282).

* * * * *